(12) United States Patent
Jamali et al.

(10) Patent No.: US 10,408,896 B2
(45) Date of Patent: Sep. 10, 2019

(54) SPINTRONIC DEVICES

(71) Applicant: University of Utah Research Foundation, Salt Lake City, UT (US)

(72) Inventors: Shirin Jamali, Salt Lake City, UT (US); Christoph Boehme, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 15/920,444

(22) Filed: Mar. 13, 2018

(65) Prior Publication Data

US 2019/0086487 A1 Mar. 21, 2019

Related U.S. Application Data

(60) Provisional application No. 62/470,741, filed on Mar. 13, 2017.

(51) Int. Cl.
| | |
|---|---|
| *H01L 23/66* | (2006.01) |
| *G01R 33/32* | (2006.01) |
| *H01L 51/50* | (2006.01) |
| *H01P 3/08* | (2006.01) |
| *H01P 11/00* | (2006.01) |

(Continued)

(52) U.S. Cl.
CPC .......... *G01R 33/323* (2013.01); *G01N 24/08* (2013.01); *H01L 23/66* (2013.01); *H01L 43/08* (2013.01); *H01L 51/0031* (2013.01); *H01L 51/0096* (2013.01); *H01L 51/05* (2013.01); *H01L 51/5012* (2013.01); *H01L 51/5088* (2013.01); *H01L 51/56* (2013.01); *H01P 3/08* (2013.01); *H01P 11/003* (2013.01); *G01R 33/24* (2013.01); *H01L 51/0035* (2013.01); *H01L 51/0036* (2013.01); *H01L 51/0037* (2013.01); *H01L 51/0038* (2013.01); *H01L 51/0047* (2013.01); *H01L 51/0081* (2013.01);
(Continued)

(58) Field of Classification Search
CPC .............................. G01R 33/323; H01L 23/66
See application file for complete search history.

(56) References Cited

U.S. PATENT DOCUMENTS

| | | |
|---|---|---|
| 6,268,695 B1 | 7/2001 | Affinito |
| 6,355,953 B1 | 3/2002 | Kirczenow |

(Continued)

FOREIGN PATENT DOCUMENTS

WO   WO 2007/132174   11/2007

OTHER PUBLICATIONS

Baker et al.; "Robust Absolute Magnetometry with Organic Thin-Film Devices." Nature Communications; Macmillian Publishers; Jun. 12, 2012; vol. 3, Article No. 898; 7 Pages.

(Continued)

*Primary Examiner* — Thomas L Dickey
(74) *Attorney, Agent, or Firm* — Thorpe North & Western, LLP

(57) ABSTRACT

A monolithic reusable microwire assembly can include a substrate and an electrically conductive thin-film wire formed on the substrate. The conductive thin-film wire can include a narrow segment forming an active area. A thermally and electrically insulating barrier can be formed on the electrically conductive thin-film wire. A roughness-reducing layer can be formed on the thermally and electrically insulating barrier and can have minimal surface roughness.

28 Claims, 18 Drawing Sheets

(51) Int. Cl.
- *H01L 51/00* (2006.01)
- *H01L 51/56* (2006.01)
- *G01N 24/08* (2006.01)
- *H01L 43/08* (2006.01)
- *H01L 51/05* (2006.01)
- *G01R 33/24* (2006.01)

(52) U.S. Cl.
CPC ...... *H01L 2223/6627* (2013.01); *H01L 2251/301* (2013.01); *H01L 2251/303* (2013.01); *H01L 2251/558* (2013.01)

(56) References Cited

U.S. PATENT DOCUMENTS

| | | | |
|---|---|---|---|
| 7,051,945 B2 | 5/2006 | Emedocles et al. | |
| 7,183,582 B2 | 2/2007 | Imamura | |
| 7,417,249 B2 | 8/2008 | Akimoto et al. | |
| 7,524,764 B2 | 4/2009 | Hirai | |
| 8,064,244 B2 | 11/2011 | Zhang et al. | |
| 8,184,411 B2 | 5/2012 | Zhang et al. | |
| 8,300,356 B2 | 10/2012 | Kunliang et al. | |
| 8,508,006 B2 | 8/2013 | Jan et al. | |
| 8,575,674 B2 | 11/2013 | Sukegawa et al. | |
| 8,592,927 B2 | 11/2013 | Jan et al. | |
| 8,872,291 B2 | 10/2014 | Sukegawa et al. | |
| 9,117,749 B1 | 8/2015 | Or-Bach et al. | |
| 9,336,937 B2 | 5/2016 | Takahashi et al. | |
| 2005/0264212 A1* | 12/2005 | Kim | H01J 11/12 313/587 |
| 2008/0135949 A1 | 6/2008 | Lo et al. | |
| 2014/0247048 A1 | 9/2014 | Cochrane et al. | |
| 2014/0368555 A1 | 12/2014 | Namkung | |

OTHER PUBLICATIONS

Boehme et al.; "Pulsed Electrically Detected Magnetic Resonance in Organic Semiconductors." Physica Status Solidi; Nov. 24, 2009; vol. 246, Issues 11-12; pp. 2750-2755.

Boehme et al.; "Coherent Defect Spectroscopy with Pulsed Optically and Electrically Detected Magnetic Resonance." Journal of Materials Science: Materials in Electronics; Springer; Oct. 2007; vol. 18, Supplement 1; pp. 285-291.

Boehme et al.; "Challenges for Organic Spintronics." Nature Nanotechnology; Macmillan Publishers; Sep. 2013; vol. 8; pp. 612-615.

Cochrane et al.; "Vectorized Magnetometer for Space Applications Using Electrical Readout of Atomic Scale Defects in Silicon Carbide." Nature Scientific Reports; Nov. 28, 2016; vol. 6; 13 Pages.

Joshi et al.; "Separating Hyperfine from Spin-Orbit Interactions in Organic Semiconductors by Multi-Octave Magnetic Resonance Using Coplanar Waveguide Microresonators." Applied Physics Letters; Sep. 2016; vol. 109, Issue 10; pp. 103303-1-103303-5.

Kawamura et al.; "Thermal Stability and Electrical Properties of Ag—Ti Films and Ti/Ag/Ti Films Prepared by Sputtering." Vacuum; Elsevier; Jan. 2013; vol. 87; pp. 222-226.

Malissa et al.; "Superconducting Coplanar Waveguide Resonators for Low Temperature Pulsed Electron Spin Resonance Spectroscopy." Review of Scientific Instruments; American Institute of Physics; Feb. 2013; vol. 84; pp. 025116-1-025116-5.

Marques et al.; "Work Function Changes in the Ag Deposition on $TiO_2$ (110)." Vacuum; Elsevier; Aug. 8, 2008; vol. 82, Issue 12; pp. 1425-1427.

Park et al.; "Low Emissivity Ag/Ta/Glass Multilayer Thin Films Deposited by Sputtering." Journal of Applied Physics; American Institute of Physics; Sep. 20, 2011; vol. 110; pp. 063508-1-063508-7.

Peng et al.; "Preparation of Nano-Ag/$TiO_2$ Thin-Film" Transactions of Nonferrous Metals Society of China; Elsevier; vol. 18, Issue 4; Aug. 2008; pp. 986-994.

\* cited by examiner

- $f \approx 85$ MHz
- Sensitivity = 100nA/V
- Low pass filter (10 Hz)
- Bias voltage = 2.8V

SPINTRONIC DEVICES

RELATED APPLICATION

This application claims the benefit of U.S. Provisional Application Ser. No. 62/470,471, filed Mar. 13, 2017, which is incorporated herein by reference.

GOVERNMENT INTEREST

This invention was made with government support under Grant No. DE-SC0000909 awarded by the Department of Energy. The government has certain rights in the invention.

BACKGROUND

Magnetic resonance of charge carrier (so called polaron) spin states in thin solid films made of π-conjugated polymers can be observed through the measurement of charge carrier recombination currents in diode devices that allow for both electron and hole polaron injection.

Such electrical detection of magnetic resonance (EDMR) is significantly more sensitive than inductively detected magnetic resonance as the resonantly measured sample current is only weakly dependent of the polaron ensemble magnetization, and thus, it is not directly dependent on the applied temperature, the magnetic field, or the sample volume. For this reason EDMR on polymer-thin film diodes has been used in the past for magnetic resonance based absolute magnetometry of mid to low magnetic field domains. Furthermore, EDMR spectroscopy at low static field $B_0$ and high driving field $B_1$ has become of fundamental interest for the exploration of nonlinear magnetic field phenomena.

SUMMARY

A monolithic reusable microwire assembly can include a substrate and an electrically conductive thin-film wire formed on the substrate. The conductive thin-film wire can include a narrow segment forming an active area. A thermally and electrically insulating barrier can be formed on the electrically conductive thin-film wire. A roughness-reducing layer can be formed on the thermally and electrically insulating barrier and can have a surface roughness of less than or equal to 20 nanometers (nm).

A monolithic spintronic device can include a monolithic reusable microwire assembly as described herein and a thin-film device formed on the monolithic reusable microwire assembly and positioned directly above the active area of the thin-film wire.

A method of manufacturing a monolithic microwire assembly can include depositing an electrically conductive thin-film microwire on a substrate and shaping the thin-film microwire to have a narrow segment forming an active area of the thin-film microwire. The method can also include depositing an electrical and thermal insulation barrier on the thin-film microwire. A roughness-reducing layer can be deposited on the electrical and thermal insulation barrier to achieve a surface roughness of less than 20 nm.

There has thus been outlined, rather broadly, the more important features of the invention so that the detailed description thereof that follows may be better understood, and so that the present contribution to the art may be better appreciated. Other features of the present invention will become clearer from the following detailed description of the invention, taken with the accompanying drawings and claims, or may be learned by the practice of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figure 1:
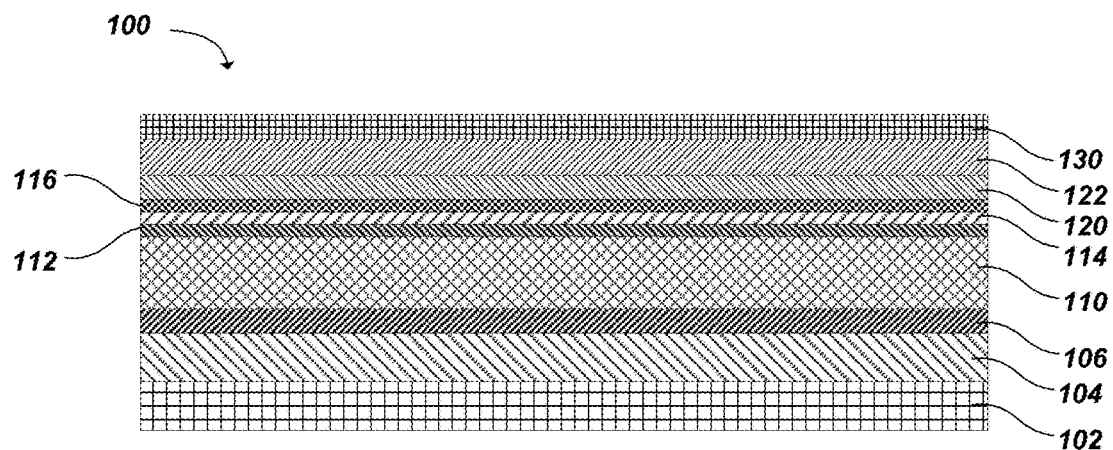
FIG. 1 illustrates a cross-sectional view of an example monolithic reusable microwire assembly, in accordance with examples of the present disclosure.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the invention, it should be understood that other embodiments may be realized and that various changes to the invention may be made without departing from the spirit and scope of the present invention. Thus, the following more detailed description of the embodiments of the present invention is not intended to limit the scope of the invention, as claimed, but is presented for purposes of illustration only and not limitation to describe the features and characteristics of the present invention, to set forth the best mode of operation of the invention, and to sufficiently enable one skilled in the art to practice the invention. Accordingly, the scope of the present invention is to be defined solely by the appended claims.

Definitions

In describing and claiming the present invention, the following terminology will be used.

The singular forms "a," "an," and "the" include plural referents unless the context clearly dictates otherwise. Thus, for example, reference to "a particle" includes reference to one or more of such materials and reference to "subjecting" refers to one or more such steps.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 5%, and most often less than 1%, and in some cases less than 0.01%.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, and combinations of each.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Spintronic Devices

As previously mentioned, magnetic resonance of charge carrier (polaron) spin states in thin films made of π-conjugated polymers can be observed by measurement of recombination currents in diode devices that allow for both electron and hole polaron injection. This is referred to as electrically detected magnetic resonance (EDMR). In contrast to inductively detected magnetic resonance spectroscopy, the sensitivity of EDMR does not depend on ensemble polarization and thus can be carried out on very small sample sizes at room temperature and at very low magnetic field conditions. These circumstances allow for investigation of very peculiar magnetic resonance parameter domains, including the regime where the amplitude of the resonant driving field $B_1$ is of the same order of magnitude as the static magnetic field, $B_0$. These "non-linear" magnetic resonance conditions are technically hard to achieve for inductively detected magnetic resonance. Additional background details are provided in G. Joshi et al. (2016), *Separating hyperfine from spin-orbit interactions in organic semiconductors by multi-octave magnetic resonance using coplanar waveguide microresonators*, Applied Physics Letters 109, 103303, which is incorporated herein by reference.

It is noted that organic light-emitting diodes (OLEDs) make exquisite probes to test magnetic resonance phenomena under unconventional conditions since spin precession controls singlet-triplet transitions of electron-hole pairs, which in turn give rise to distinct recombination currents in the conductivity. Magnetic resonance can therefore be recorded in the absence of spin polarization. This characteristic can be exploited to explore the exotic regime of ultrastrong light-matter coupling, where the Rabi frequency of a charge carrier spin is of order the transition frequency of the two-level system. To reach this domain, the Zeeman splitting of the spin states can be lowered, defined by the static magnetic field $B_0$, and the oscillatory driving field of the resonance, $B_1$, can be raised. This can be achieved by shrinking the OLED and bringing the source of resonant radio-frequency (RF) radiation as close as possible to the organic semiconductor in a monolithic device structure that incorporates an OLED fabricated directly on top of an RF stripline within one thin-film structure. With driving power of the RF stripline the mW range the regime of bleaching and inversion of the magnetic resonance signal is reached due to the onset of the spin-Dicke effect, where the individual spin transitions of electron-hole pairs become indistinguishable with respect to the driving field and superradiance sets in.

The underlying concept of many approaches to quantum information processing by singlet-triplet qubits relies on initialization, control, and readout of the permutation symmetry of a pair of spins. Examples of this approach include electrostatically defined coupled quantum dots in GaAs, silicon, or in carbon nanotubes, but also in isolated spins of unpaired electrons in bulk crystals, the most prominent example being the diamond nitrogen-vacancy system. In parallel to these developments, evidence has been emerging that the magnetoceptive abilities of some migratory avian species also rely on the coherent interconversion between singlet and triplet states of photoinduced radical pairs formed in retinal pigment-protein complexes. Such interconversion is driven by local hyperfine fields and modified by Earth's static magnetic field. It appears to be so robust to dephasing influences that it can even be perturbed by the oscillating fields of ambient anthropogenic electromagnetic noise. OLEDs operate by the electrical injection of positive and negative charges and therefore make unique solid-state systems to study the interconversion of singlet and triplet recombinant carrier pairs. Such recombination can be detected either in electroluminescence or in the device current, which has proven sufficiently sensitive to monitor even miniscule perturbations in the resonantly controlled nuclear spin ensemble. Nuclear magnetic resonance imparts perturbations of electronic transport on energy scales as small as a millionth of kT, but is still resolved in picoampère changes to device current. The unique appeal of coherent spin electronics in OLEDs is that experiments can, in principle, be carried out at arbitrary resonance frequencies and temperatures. This fact has led to the realization of ultrastrong light-matter coupling in the driving of singlet-triplet pair transitions, e.g. the emergence of the non-perturbative regime of magnetic resonance where the Rabi frequency approaches the energetic separation of spin eigenstates. This regime, which leads to the formation of a new singlet-triplet basis of spin wavefunctions, can be analogous to the emergence of superradiant collectivity of optical dipole transitions in the Dicke effect: When the DC magnetic field $B_0$ that is applied to the spin ensemble is larger than the inhomogeneous broadening and the oscillating driving field $B_1$ exceeds $B_0$, the individual spins become indistinguishable and interact collectively with the driving field.

Reaching this unique spin coherence regime necessitates that $B_1$ becomes comparable to the Zeeman field defining the spin levels, $B_0$. In some cases, this threshold can be reached by using custom-designed nuclear magnetic resonance (NMR) coils surrounding the OLED. This "brute force" approach, however, requires extremely high electrical powers, which can lead to excessive heat formation, which can be hard to dissipate and can ultimately destroy the OLED. An alternative approach can use superconducting stripline resonators to achieve $B_1 \approx B_0$. However, this method comes with the requirement of low temperatures, where a range of additional magnetic resonance features can arise due to long-lived triplet excitons, and also makes pulsing of the $B_1$ field prohibitive because of the extremely high Q-factors of these resonators. Pulsing of $B_1$ is desirable since it allows the detection of coherent Rabi nutation in the device current, which provides an absolute measurement of the magnitude of the local $B_1$ field acting on the device.

The present disclosure is directed to a new device structure to probe the ultrastrong coupling regime at room temperature by optimizing two aspects of resonantly driving OLEDs: minimizing field inhomogeneity by shrinking the active device or active site area to a small diameter (e.g. from about 40 µm to about 80 µm, or 57 µm in one specific example) and at the same time optimizing coupling of the $B_1$ field to the OLED in an architecture combining a stripline RF source and an OLED in one monolithic thin-film device.

Generally, the spintronic device disclosed herein can include a reusable monolithic base layer or microwire assembly that can be purposed and/or re-purposed with any suitable organic thin film device fabricated or grown thereon. By monolithic, it is to be understood that a monolithic assembly or device is formed as a single unitary assembly or device (e.g. layer-by-layer, for example), rather than as separate individual components that are subsequently interconnected or integrated together. The monolithic reusable microwire assembly can include a substrate and an electrically conductive thin-film wire formed on the substrate. As described above, the conductive thin-film wire can include a narrow segment forming a narrow active area, which can facilitate room temperature measurements with the device. The narrow active area is thus bounded on either end by wider large area thin-film wire portions. These wider areas can also aid in heat dissipation and provide larger contacts for electrical connections. A thermally and electrically insulating barrier can be formed on the electrically conductive thin-film wire. A roughness-reducing layer can be formed on the thermally and electrically insulating barrier and can have a surface roughness of less than or equal to 20 nanometers (nm).

One non-limiting example of a monolithic reusable microwire assembly 100 is illustrated in FIG. 1. The monolithic microwire assembly 100 can include a substrate 102, such as a silicon substrate, quartz substrate, glass, plastic, or other suitable substrate. In some examples, the substrate 102 can include or be formed of a material that is suitable for use as a heat drain for the microwire 110. Accordingly, in some examples, the substrate 102 can be positioned sufficiently proximate to the microwire 110 to reasonably function as a heat drain for the microwire 110. In some additional examples, the substrate 102 is not thermally isolated from the thin-film microwire 110 to allow the substrate to function as a heat drain for the microwire 110. The thickness of the substrate is not particularly limited and can be adjusted as desired. In one non-limiting example, the substrate can have a thickness ranging from about 50 μm to about 2000 μm, and most often 100 μm to 500 μm.

In some specific examples, the substrate can include a substrate adhesion layer, or have a substrate adhesion layer formed thereon, to facilitate adhesion of subsequently formed layers to the substrate. In some examples, the substrate adhesion layer can also provide electrical and/or thermal insulation, as desired. A variety of suitable substrate adhesion layers can be used. In some examples, the substrate adhesion layer can include an oxide or nitride dielectric material. In some specific examples, the substrate adhesion layer can include or be formed of $SiO_2$. Other materials such as silicon nitride, or metallic adhesion layers such as Ti, Cr, are also suitable. The substrate adhesion layer can be formed or deposited on the substrate or as part of the substrate in a variety of ways, such as by a suitable deposition technique (e.g. PVD, CVD, ALD, the like, or a combination thereof), thermal oxidation, the like, or a combination thereof. The substrate adhesion layer can have a variety of suitable thicknesses. In one non-limiting example, the substrate adhesion layer can have a thickness of from about 20 nm to about 100 nm. As a general guideline, thinner substrate adhesion layers are desirable.

In some further examples, a diffusion barrier layer 104 can be included as part of the substrate or deposited on the substrate. The diffusion barrier layer can be formed of any suitable dielectric material that can act as a diffusion barrier for adjacent layers or materials. In one specific examples, the diffusion barrier layer can include or be formed of SiN. The diffusion barrier can typically be deposited by chemical vapor deposition (CVD), physical vapor deposition (PVD), atomic layer deposition (ALD), the like, or a combination thereof. The diffusion barrier layer can also typically have any suitable thickness. In one non-limiting example, the diffusion barrier layer can have a thickness from about 100 nm to about 300 nm, or from about 150 nm to about 250 nm, and in some cases about 150 nm.

In some examples, a thin-film wire adhesion layer 106 can be added to the substrate 102 or diffusion barrier layer 104 to facilitate adhesion of the thin-film wire 110 to the substrate or intervening layer. In some specific examples, the thin-film wire adhesion layer can include or be formed of titanium or chromium. The thin-film wire adhesion layer can be deposited via a variety of deposition techniques. In some examples, the thin-film wire adhesion layer can be deposited by CVD, PVD such as sputtering, thermal evaporation, e-beam evaporation, ALD, or the like. This thin-film wire adhesion layer can have any suitable thickness. In one non-limiting example, the thin-film wire adhesion layer can have a thickness of from about 1 nm to about 100 nm, or from about 5 nm to about 50 nm, or from about 10 nm to about 30 nm. Often, a desired thickness can depend on a thickness of an adjacent copper top layer. For example, thickness can be adjusted based on electrical conductivity of the adhesion layer (e.g. which is lower than adjacent copper), in order to relieve internal mechanical stress, and the like.

The electrically conductive thin-film wire 110 can be deposited on the substrate 102, adhesion layer 106, or other intervening layer. The thin-film wire 110 can be made of a variety of suitable materials, such as copper, indium tin oxide, gold, niobium, aluminum, tungsten, or other suitable materials, any metals or superconductors or any conductive material. However, it is noted that the thin-film wire typically cannot be placed in the furnace during manufacture of the monolithic microwire. The thin-film wire can typically be deposited via sputtering, electroplating, electron beam evaporator, thermal evaporator, or the like. However, other methods of depositing an electrically conductive material to form a thin-film microwire can also be used. The thin-film wire can have a variety of suitable thicknesses. In one non-limiting example, the thin-film wire can have a thickness from about 700 nm to about 1400 nm, or from about 800 nm to about 1200 nm, or from about 900 nm to about 1100 nm. The thickness can also range from 50 nm to 4 microns, where thickness can depend on a desired magnitude of a radio frequency amplitude, as well as microwire geometry.

In some examples, an additional, or upper, thin-film wire adhesion layer 112, such as a titanium adhesion layer, chromium, or other suitable adhesion layer, can be deposited on the thin-wire layer 110. The upper thin-film wire adhesion layer can be deposited via a variety of deposition techniques. In some examples, the upper thin-film wire adhesion layer can be deposited by sputtering, thermal or electron beam evaporator, or any other physical vapor deposition techniques, the like or a combination thereof. In other examples, the upper thin-film wire adhesion layer can be deposited via sputtering, or other PVD techniques. This upper adhesion layer 112 can also have a variety of thicknesses. In one non-limiting example, the adhesion layer can have a thickness of from about 0.5 nm to about 20 nm, or from about 1 nm to about 10 nm. The thickness can generally depend on a thickness of a following top layer. In some examples, the upper thin-film wire adhesion layer can optionally be oxidized to improve work function and make the active area surface hydrophilic. This treatment for 1 nm to 4 nm of Ti on gold particularly improves the adhesion of gold and PEDOT-PSS that is widely used for fabrication of OLED.

In some further examples, an etch stop layer 114 can be applied to the thin-film wire 110 or upper adhesion layer 112. The etch stop layer can include gold, silver or other suitable etch stop material for lateral structuring. The etch stop layer can be deposited via a variety of deposition techniques. In some examples, the thin-film wire adhesion layer can be deposited by sputtering, evaporators or other PVD techniques the like or a combination thereof. In other examples, the etch stop layer can be deposited via sputtering, or the like. This layer can have a variety of thicknesses. In one non-limiting example, the etch stop layer can have a thickness from about 1 nm to about 15 nm, from about 3 nm to about 10 nm, or from about 5 nm to about 9 nm.

In still further examples, yet another adhesion layer 116, such as a titanium adhesion layer, chromium, or other suitable adhesion layer, can be applied to the etch stop layer 114. It is also noted that this layer can be oxidized, as desired, to form a titanium oxide layer or other suitable oxide layer. The adhesion layer can be deposited via a variety of deposition techniques. In some examples, the adhesion layer can be deposited by CVD, PVD, ALD, the like or a combination thereof. In other examples, the adhesion layer can be deposited via sputtering, or the like. This adhesion layer 116 can have a variety of thicknesses. In one non-limiting example, this adhesion layer can have a thickness of from about 1 nm to about 25 nm, about 5 nm to about 20 nm, or about 6 nm to about 10 nm or 15 nm.

A thermally and electrically insulating barrier can be formed on the thin-film wire 110, the adhesion layer 116, or other intervening layer. In some examples, the thermally and electrically insulating barrier can be formed of one or more layers, such as SiN layer 120 and SiO$_2$ layer 122, for example, or other suitable insulating layer(s) for electrical and thermal insulation such as aluminum oxide and electrically insulating oxides. Where an SiN layer 120 is used, the layer can have any suitable thickness. In one non-limiting examples, the SiN layer 120 can have a thickness from about 120 nm to about 250 nm, or from about 150 nm to about 200 nm. Where an SiO$_2$ layer 122 is used, this layer can also have any suitable thickness. In one specific example, the SiO$_2$ layer 122 can have a thickness from about 500 nm to about 1500 nm, or from about 800 nm to about 1200 nm, or from about 900 nm to about 1000 nm or 1100 nm. However, it is noted that any suitable number of layers can be used to form the thermally and electrically insulating layer(s). In some examples, a single thermally and electrically insulating layer can be used. In other examples, two or more thermally and electrically insulating layers can be used. It is further noted that, in some cases, some layer(s) can be applied to provide thermal insulation and other layer(s) can be applied to provide electrical insulation. The thermally and electrically insulating barrier can be formed in a variety of ways. For example, the thermally and electrically insulating barrier can be deposited via a variety of deposition techniques, such as PECVD, PVD, ALD (Al$_2$O$_3$), the like or a combination thereof. SiN is particularly useful as a diffusion barrier for copper. In addition to its insulating properties, SiO$_2$ acts as the adhesion surface for the next layer, e.g. spin on glass.

A roughness-reducing layer 130 can be deposited on the one or more thermally and electrically insulating layers, such as layers 120 and 122. The roughness-reducing layer can be a spin on glass (SOG) layer, a parylene layer, or other suitable layer to decrease the roughness of the monolithic reusable microwire assembly 100. Cured photoresist can also be used. The roughness-reducing layer 130 can have any suitable thickness. In one non-limiting example, the roughness-reducing layer can have a thickness from about 50 nm to about 1500 nm, from about 60 nm to about 500 nm or 1000 nm, or from about 70 nm to about 250 nm. The roughness reducing layer can provide a low surface roughness to the monolithic microwire and associated spintronic device. In some examples, the surface roughness can be less than 100 nm, less than 50 nm, less than 20 nm, less than 10 nm, less than 5 nm, and in some cases less than 1 nm. As used herein, surface roughness generally refers to peak to valley roughness or vertical displacement as measured by a profilometer. The roughness-reducing layer can be deposited in a variety of ways. In some examples, the roughness-reducing layer can be spin-coated on the thermally and electrically insulating barrier. In other examples, the roughness-reducing layer can be deposited via Parylene coater, the like, or a combination thereof. Any suitable deposition technique that can achieve a minimal surface roughness can be employed. The roughness-reducing layer can provide sufficient smoothness for back electrical contacts of a subsequently formed thin-film device to minimize or prevent vertical shorts.

In some examples, an intermediary roughness-reducing layer (not shown) can be formed between the thermally and electrically insulating barrier and the roughness-reducing layer to reduce surface roughness prior to application of the roughness-reducing layer. For example, surface roughness can be reduced to less than or equal to a thickness of the top layer. As one non-limiting example, a 100 nm SiN layer can be applied to the thermally and electrically insulating barrier and etched (e.g. via reactive ion etching) to minimize surface roughness of the thermally and electrically insulating barrier prior to application of the roughness-reducing layer.

It is also noted that the monolithic reusable microwire can be further etched to form windows for electrical contacts to the thin-film wire. This can facilitate electrical connections for subsequently formed device components.

The monolithic reusable microwire assembly can be used, and subsequently re-purposed, with any suitable thin-film device to form a monolithic spintronic device. Generally, a monolithic spintronic device can include a monolithic reusable microwire assembly as described herein and a thin-film device formed on the monolithic reusable microwire assembly. The thin-film device can be positioned directly above the active area of the thin-film wire of the monolithic reusable microwire assembly.

Figure 2:
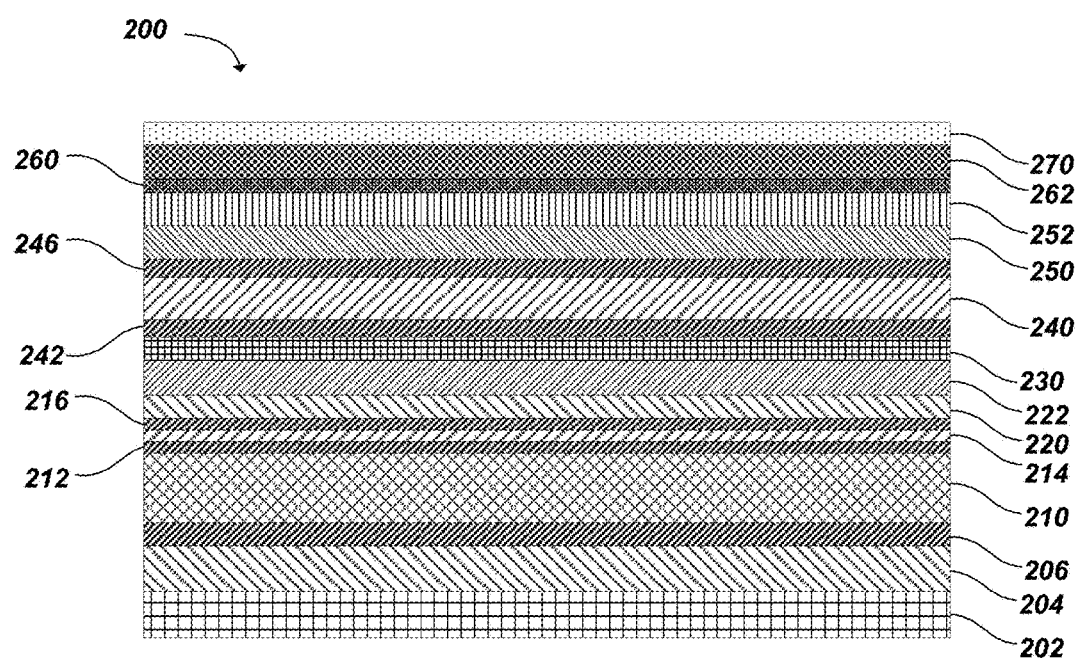
FIG. 2 depicts a cross-sectional illustration of a spintronic device, in accordance with examples of the present disclosure.

One specific example of a monolithic spintronic device 200 is illustrated in FIG. 2. It is noted that FIG. 2 illustrates a cross-sectional view of the monolithic spintronic device within the vertical active area of the device with the thin-film device positioned directly above the active area of the thin-film wire. As such, additional lateral features positioned outside of the active area of the monolithic spintronic device are not depicted in this drawing. In further detail, the spintronic device can include a monolithic reusable microwire assembly including a substrate 202, diffusion barrier layer 204, thin-film wire adhesion layer 206, conductive thin-film wire 210, upper thin-film wire adhesion layer 212, etch stop layer 220, etch-stop adhesion layer 220, electrically and thermally insulating layers 220 and 222, and roughness-reducing layer 230, as described previously.

An electrical contact layer 240 can be formed on the roughness-reducing layer 230. The electrical contact layer 240 can be positioned and configured to electrically connect with a subsequently formed thin-film device. The electrical contact layer 240 can be formed of any suitable electrically conductive material. In some specific examples, the electrical contact layer can be formed of gold, silver, indium, aluminum, niobium, or the like, or a combination thereof. The electrical contact layer 240 can be deposited or formed in a variety of ways. Typically, the electrical contact layer can be deposited via sputtering. However, other suitable deposition techniques can also be used. For example, one simple approach is using silver paint or indium dots. The electrical contact layer can have a variety of thicknesses. In some examples, the electrical contact layer can have a thickness of from about 20 nm to about 200 nm, or from about 50 nm to about 100 nm. It is further noted that, in some examples, the electrical contact layer 240 can also form part of the monolithic reusable microwire assembly.

In some additional examples, an electrical contact adhesion layer 242 can be formed or deposited between the roughness-reducing layer 230 and the etch-stop layer 240. In some specific examples, the electrical contact adhesion layer 242 can include or be formed of titanium or chromium. The electrical contact adhesion layer 242 can be deposited via a variety of deposition techniques. In some examples, the electrical contact adhesion layer can be deposited by CVD PVD, ALD, the like or a combination thereof. In other examples, the electrical contact adhesion layer can be deposited via sputtering, evaporating and other PVD technics or the like. The electrical contact adhesion layer can have any suitable thickness. In one non-limiting example, the electrical contact adhesion layer can have a thickness of from about 1 nm to about 50 nm, or from about 5 nm to about 20 nm, or from about 8 nm to about 15 nm.

In some further examples, an upper electrical contact adhesion layer 246 can be formed or deposited on the electrical contact layer 240. In some specific examples, the upper electrical contact adhesion layer 246 can include or be formed of titanium or chromium. The upper electrical contact adhesion layer 246 can be deposited via a variety of deposition techniques. In some examples, the upper electrical contact adhesion layer can be deposited by CVD, PVD, ALD, the like or a combination thereof. In other examples, the upper electrical contact adhesion layer can be deposited via sputtering, or the like. The upper electrical contact adhesion layer can have any suitable thickness. In one non-limiting example, the upper electrical contact adhesion layer can have a thickness of from about 0.5 nm to about 50 nm, or from about 1 nm to about 10 nm, or from about 1.5 nm to about 5 nm. It is further noted that, in some examples, one or more of the electrical contact adhesion layer 242 and the upper electrical contact adhesion layer 246 can also form part of the monolithic reusable microwire assembly.

In the example illustrated in FIG. 2, the thin film device is an organic light-emitting diode (OLED) formed of two layers 250, 252. Layer 250 is a hole injector layer. The hole injector layer 250 can be formed of a variety of materials suitable for hole injection. One non-limiting example can include poly(styrene-sulfonate)-doped poly(3,4-ethylenedioxythiophene) (PEDOT:PSS). The hole injector layer 250 can be spin-coated, or otherwise deposited, on the electrical contact layer 240, or other intervening layer (e.g. upper electrical contact adhesion layer 246). The hole injector layer can have a variety of thicknesses. For example, in some cases, the hole injector layer can have a thickness of from about 50 nm to about 200 nm, or from about 70 nm to about 150 nm, or from about 80 nm to about 120 nm.

Layer 252 is an emitting layer. The emitting layer 252 can be formed of a variety of materials suitable for light emission. One non-limiting example can include super-yellow poly(phenylene-vinylene) (SY-PPV). Other organic semiconductors can be used like MEHPPV (partially and fully deuterated), PCBM, $P_3HT$, $Alq_3$, PFO and others, also other inorganic semiconductor. The emitting layer 252 can be spin-coated, or otherwise deposited, on the hole-injection layer 250. The emitting layer can have a variety of thicknesses. For example, in some cases, the emitting layer can have a thickness of from about 50 nm to about 200 nm, or from about 70 nm to about 150 nm, or from about 80 nm to about 120 nm.

A cathode can be formed on the OLED thin-film device. The cathode can include layers 260, 262, for example. Lower cathode layer 260 can represent a calcium layer and upper cathode layer 262 can represent an aluminum layer. However, any other suitable cathode materials can be used. For example, LiF and Al also can be used. As a general guideline, the work function of the material should match with the conduction energy band of the polymer. The cathode layers can be deposited via a variety of techniques. In some examples, the cathode layers can be deposited by thermal vacuum evaporation, electron beam physical vapor deposition, the like, or a combination thereof. The cathode layers can have a variety of thicknesses. In some examples, the lower cathode layer 260 can have a thickness of from about 0.5 nm to about 50 nm, from about 1 nm to about 20 nm, or from about 5 nm to about 10 nm. In some additional examples, the upper cathode layer 262 can have a thickness of from about 50 nm to about 500 nm, from about 70 nm to about 250 nm, or from about 100 nm to about 200 nm.

An encapsulating film, such as an epoxy or other suitable encapsulating material, can be used to form an encapsulating layer 270 on the cathode. Spin on glass and high vacuum grease also can be used. The encapsulating layer 270 can have any suitable thickness for encapsulating the monolithic spintronic device.

Figure 3A:
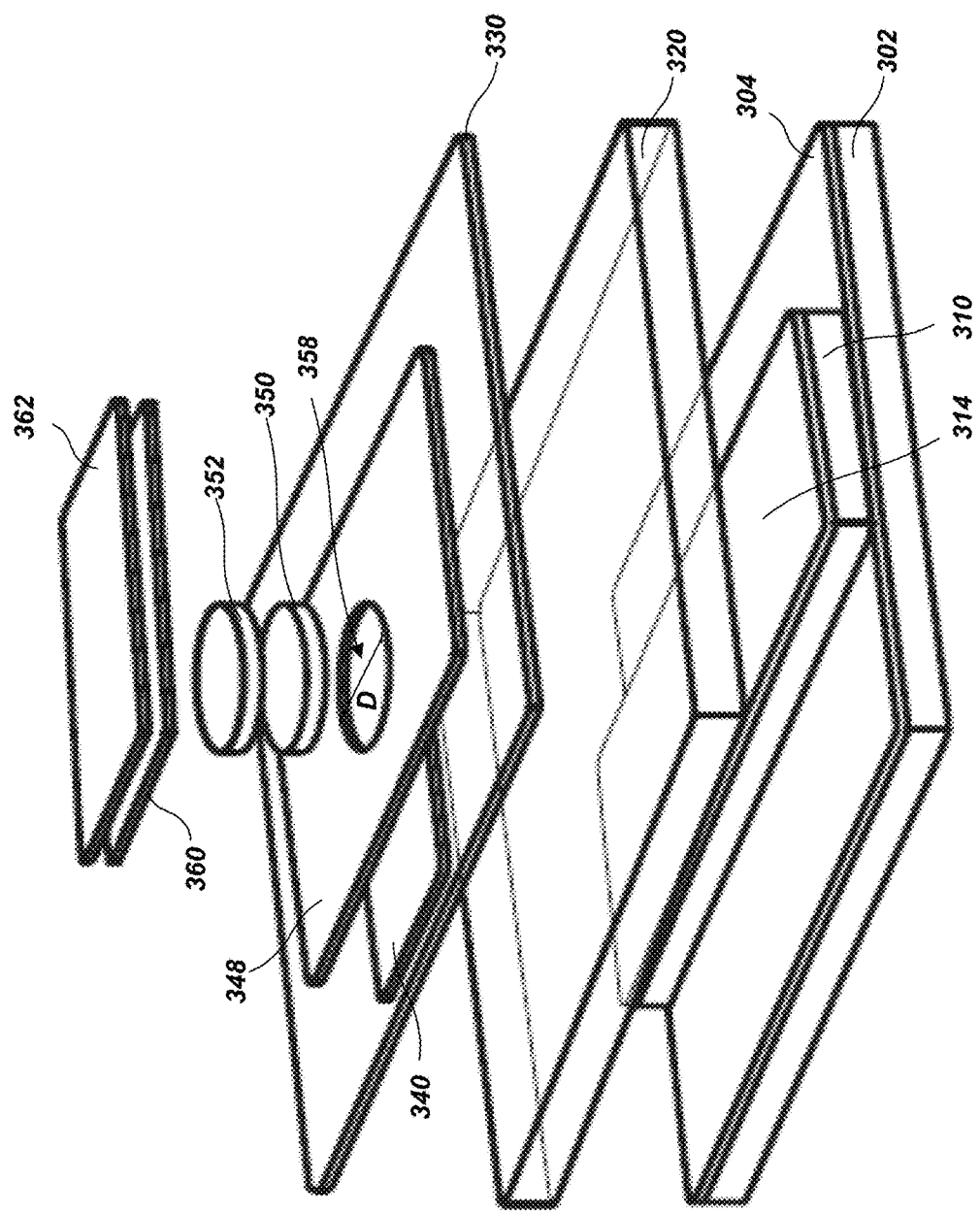
FIG. 3A illustrates a vertical stack structure of the layers used to make up a spintronic device, in accordance with examples of the present disclosure.

FIG. 3A shows one exemplary spintronic device structure in further detail. The monolithic spintronic device 300 can include a variety of layers and features, such as those described with respect to FIGS. 1 and 2. Specifically, monolithic spintronic device 300 can include a substrate 302 and a diffusion barrier 304, such as those described elsewhere herein. The monolithic spintronic device 300 can also include a thin-film microwire 310 deposited on the diffusion barrier layer 304. An etch stop layer 314 can be formed on the thin-film microwire 310. A thermally and electrically insulating barrier 320 can be formed on the etch stop layer 314. A roughness-reducing layer 330 can be formed on the thermally and electrically insulating barrier 320. An electrical contact layer 340 can be formed on the roughness-reducing layer 330. A photoresist layer 348 can be formed on the electrical contact layer 340. An active site 358 can be formed in the photoresist layer 348 within an active area of the device (i.e. directly above a narrow segment of the thin-film microwire (See FIG. 3B)). The active site 358 can have a narrow diameter D to accommodate a thin-film device within the active site also having a narrow diameter. In some examples, the diameter D can be from about 20 μm to about 100 μm, about 30 μm to about 80 μm, or about 40 μm to about 70 μm. It is noted that, in some examples, the thin-film device can also have a diameter of from about 20 μm to about 100 μm, about 30 μm to about 80 μm, or about 40 μm to about 70 μm. In some specific examples, the thin-film device can have a diameter of from about 50 μm to about 60 μm or 65 μm. A thin-film device, such as an OLED formed of hole injector layer 350 and emitting layer 352, can be deposited within the active site 358 on the electrical contact layer 340. Thus, different metallic, dielectric, and adhesive layers can be used to ensure sufficient electrical and thermal conductivity of the RF stripline (i.e. thin-film microwire), electrical isolation from the OLED, and smoothing of the OLED bottom contact to prevent vertical shorts.

Figure 3B:
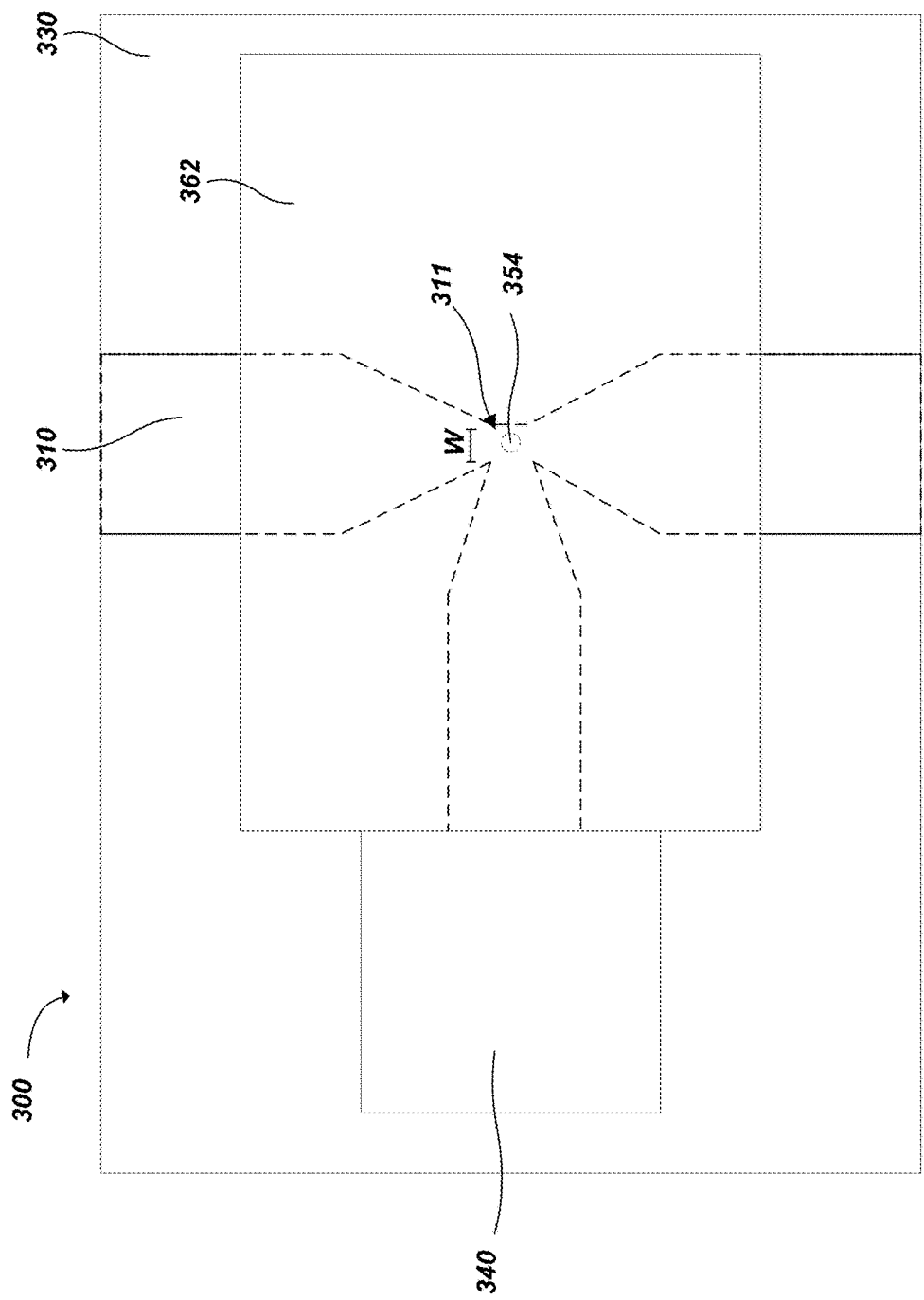
FIG. 3B depicts top plan view of the device of FIG. 3A, in accordance with examples of the present disclosure.
Figure 3C:
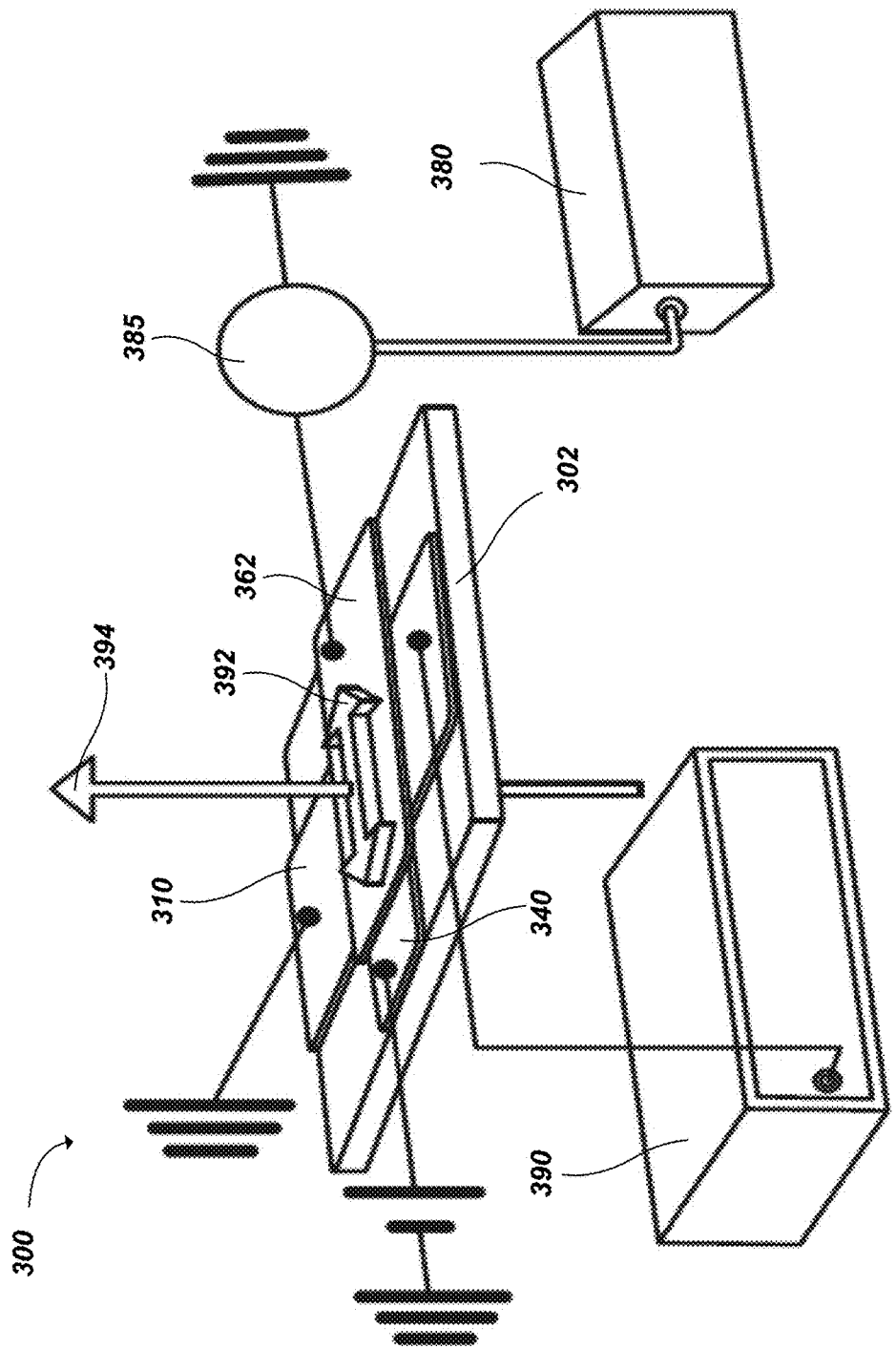
FIG. 3C depicts an schematic illustration of an example experimental measurement configuration using a spintronic device of according to FIG. 3A, with the resonant driving field $B_1$ and the Zeeman field of the spin states $B_0$ indicated, in accordance with examples of the present disclosure.

In this particular example, the template structure (i.e the monolithic reusable thin-film microwire assembly) of the device is fabricated up to the step of the photoresist (PR) layer 348 under cleanroom conditions. The OLED active layers, the hole injector layer 350 poly(styrene-sulfonate)-doped poly(3,4-ethylenedioxythiophene) (PEDOT:PSS) and the emitting layer 352 super-yellow poly(phenylene-vinylene) (SY-PPV) or any other organic semiconductor are spin-coated in a nitrogen-filled glovebox and subsequently contacted with a cathode layer of calcium and aluminum deposited by thermal evaporation under high vacuum. Material with low magnetic hyperfine fields are particularly useful as it will increase the sensitivity of magnetometer as it generate narrower magnetic resonance linewidth. Inorganic semiconductor such as Si can also deposited by sputtering or PECVD or any other deposition technics instead of organic semiconductor. A top plan view of the monolithic spintronic device structure is shown in FIG. 3B. The thin-film wire 310 used to generate the RF radiation runs vertically across the image and is shrunk down to form a narrow segment 311 having a width W of from about 50 µm to about 300 µm, from about 100 µm to about 200 µm, from about 125 µm to about 175 µm, or about 150 µm, beneath the OLED thin film device 354. The thin-film microwire is electrically and thermally isolated from the OLED by a thick thermally and electrically insulating barrier 320 (e.g. layer of $SiO_2$), roughness-reducing layer 330 (e.g. spin-on glass (SOG)), and optional photoresist layer 348 (e.g. for top electrode). The bottom electrode 340 of the OLED can be made of gold and can protrudes horizontally to the left of the thin-film microwire 310, as illustrated in FIG. 3B. As illustrated in FIG. 3C, an RF source 390 can be connected to the thin-film wire 310, generating an oscillating $B_1$ field 392 in the plane of the OLED. The static magnetic $B_0$ field 394 can be applied orthogonally to this field. The direct current flowing through the OLED can be measured using an analogue to digital converter (ADC) and a data acquisition (DAQ) system 380, a transient recorder. In some examples, the system 380 can be connected to the spintronic device 300 via a current amplifier 385. The OLEDs are driven in forward bias and the current change under static ($B_0$) and oscillating ($B_1$) magnetic field can be recorded at room temperature.

Figure 3D:
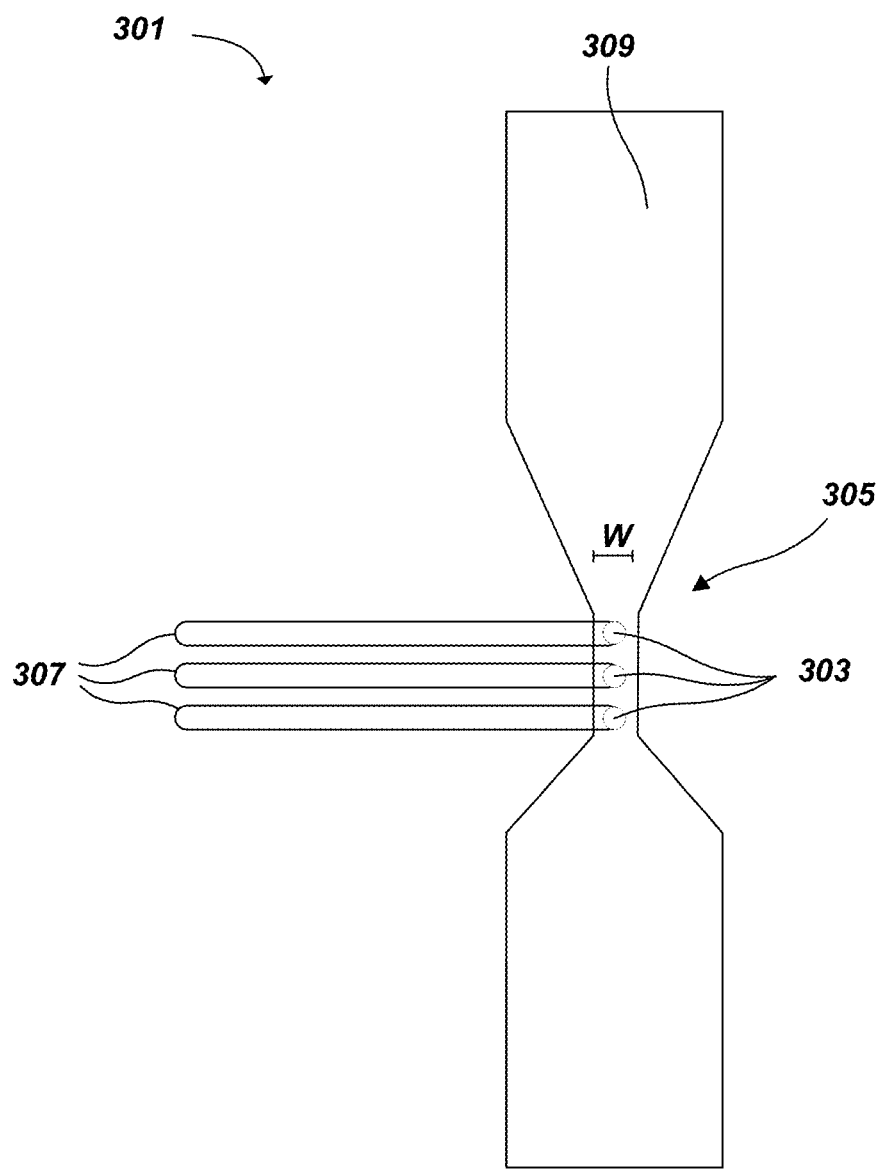
FIG. 3D is a schematic illustration of a spintronic device having multiple thin film devices integrated into a common active area in accordance with a specific example of the disclosure.

As will be recognized, these are merely examples of a device that can be manufactured using the monolithic thin-film microwire described herein. There are numerous other possible thin-film devices, such as OLED, LED (made of semiconductors such as SiC, amorphous Si) devices, that can be grown on top of the monolithic microwire. In another example, a second thin film microwire device can be deposited on top of and perpendicular to the first microwire having intersecting active areas. This configuration can be used for RF generation with arbitrary polarization states or can provide $B_0$ modulation and off set fields. Typically, such a configuration also requires that the magnetic field $B_1$ for each thin film device is equal. This can be accomplished by varying geometry and/or materials according to well-known parameters. For example, besides constituting micron-scale versatile magnetometers, which provide an absolute measure of the magnetic field by measuring the resonance frequency, these monolithic OLED-stripline structures introduced here offer versatile structures to easily reach a state of collective spin precession in OLEDs, in which all spins precess coherently in phase. Since it is the electromagnetic field which induces this coherence, the demonstration of on-chip pixel-size spin collectivity provides a means to position multiple individual devices to be driven by the same field. For example, as illustrated in FIG. 3D, a multi-device assembly 301 can include multiple thin-film devices 303 within a common active area 305 of a conductive thin-film wire 309. The multiple thin-film devices can be oriented within the narrow segment. The multiple thin-film devices can be oriented in a one-dimensional series or in multiple layers forming a two or three dimensional array. Furthermore, each thin-film device can include a dedicated electrode 307 and corresponding counter-electrodes (not shown for clarity). As with other coherent quantum systems such as atomic gases in cavities, it may be possible to entangle the collective Dicke state of one pixel—measured through the device current—with that of an adjacent pixel, driven by the same field. Such a manifestation can provide a unique experimental approach to room-temperature macroscopic coherence phenomena with all the benefits associated with the facile tunability of both spin-orbit coupling and hyperfine fields of organic semiconductors. Thus, the devices described herein can be used in a wide variety of applications, such as for an AC magnetic field source for organic semiconductor-based monolithic magnetic resonance magnetometer devices, AC magnetic field source for electrically detected magnetic resonance spectroscopy, AC magnetic field source for optically detected magnetic resonance spectroscopy, OLED, light emitting diodes, magnetometers, solar cells, resistors, capacitors, and other suitable applications. For example, the devices described herein can be generally used for magnetometery, EPR spectroscopy, vectorized magnetic field measurements of planetary bodies, and other suitable sensory measurements, such as those described in U.S. patent application Ser. No. 14/050,605, filed Oct. 10, 2013, which is incorporated herein by reference. Furthermore, devices prepared using these principles can be formed as absolute magnetic field sensors which do not require calibration for accurate measurement of magnetic fields or highly scaled micro-electron spin resonance or electrically detected magnetic resonance spectrometers or other applications which are based on the application of electromagnetic radiation with very high amplitudes or localized static or quasi-static magnetic fields such as low-frequency magnetic field modulations.

The present disclosure also describes a method of manufacturing a monolithic thin-film microwire assembly. The method can include depositing an electrically conductive thin-film microwire on a substrate and shaping the thin-film microwire to have a narrow segment forming an active area of the thin-film microwire. The method can also include depositing an electrical and thermal insulation barrier on the thin-film microwire. A roughness-reducing layer can be deposited on the electrical and thermal insulation barrier to achieve a surface roughness of less than 20 nm.

Various methods of depositing the different layers of the monolithic thin-film microwire assembly are described elsewhere herein. Shaping the thin-film microwire to have a narrow segment forming an active area of the thin-film microwire assembly can be performed in a variety of ways. For example, in some cases, the thin-film microwire can be etched to recess or narrow a portion of the thin-film microwire to have a narrow width, such as from about 50 µm to about 300 µm, from about 100 µm to about 200 µm, from about 125 µm to about 175 µm, or about 150 µm. This narrow segment of the microwire can form an active area of the device. Further, as described herein, the narrow segment can facilitate spintronic measurements at room temperature. In some specific details, the thin-film microwire can be shaped to have a narrow segment via photolithography, wet etching, lift-off, the like, or a combination thereof.

EXAMPLES

Example 1—Fabrication of a Spintronic Device

The following example describes the fabrication of monolithic copper-based lithographically defined wires for broadband (low-Q) EPR excitation located 1 micron beneath organic light emitting diode (OLED) stacks with a circular surface area of 57 µm diameter that allow for high $B_1$ and low $B_0$ EDMR spectroscopy. As a brief overview, for the fabrication of these integrated resonator/OLED devices, crossed wires were deposited on top of a quartz substrate, followed by the deposition of a 1 micron thick dielectric insulator stack below an OLED back contact. These template structures where brought into an inert glovebox environment where the OLED device layers were deposited.

In further detail, the substrate was selected according to the spectroscopy requirements, for example quartz for simultaneous optical and electrical magnetic resonance detection and silicon wafer for high power excitation. The first step is to cover the silicon wafer with oxide layer in a thermal oxidation furnace. The thermal oxidation of silicon produces a great insulating layer on silicon wafer. Dry thermal oxidation by diffusion of $O_2$ gas in Si wafer for 50 nm $SiO_2$ was obtained in the furnace at 800° C. to 1000° C. Film thickness was calculated based on the interference spectra generated when the light passes thru the film using NANOSPEC.

A low stress 200 nm SiN film at 800° C. was then deposited on the wafer using Low Pressure Chemical Vapor Deposition (LPCVD). This layer is used as diffusion barrier for a subsequently formed copper layer. The thickness of SiN was measured to be 200 nm using NANO SPEC.

Microwire was then deposited via denton sputtering in which Argon plasma at 3 mTorr detaches particles from a target material for deposition on the substrate. Denton sputter was used to deposit the following layers: a 20 nm titanium (Ti) adhesion/diffusion barrier, a 1 µm copper (Cu) microwire, a 5 nm Ti adhesion layer, a 5.6 nm gold (Au) etch stopper/electrical contact, and an 8 nm Ti adhesion layer. The thickness of the microwire was measured using profilometer to be 1 µm.

Photolithography was then performed to further define the microwire. Specifically, a hexamethyldisilazane (HDMS)/xylene (20:80) adhesion promotor for the photoresist was deposited at 3000 rpm for 60 seconds. A positive photoresist 1813 was then deposited at 3000 rpm for 60 seconds and soft baked on a hotplate at 110° C. for 1 minute. The wafer was aligned with the mask using an SUS aligner and exposed to ultraviolet radiation for 20 seconds. Subsequently the wafer was dipped into a 1:1 AZ developer for 45 seconds, rinsed with deionized water, and dried under nitrogen. The wafer was post-baked on a hotplate at 100° C. for 2 minutes.

The wafer was then cut in half using a programmable silicon dicing saw (Disco DAD641) to achieve clean etching around the microwire. The etcher container was placed on top of a hotplate with a temperature sensor inside the container and with a magnetic stir bar rotating at 200 rpm to achieve uniform etching. A buffered oxide etch (BOE) was performed at 27° C. for 1 minute. The wafer was then dipped in a commercial Au etch for 5 seconds. A BOE etch was repeated 27° C. for 40 seconds. The Cu was then etched using a chromium etch at 27° C. for 2.5 minutes. After each step, the wafer was thoroughly rinsed with deionized water. It is noted that in some cases residual particles can stick to the surface, especially around the edges of the microwire. Spraying or immersing the wafer in deionized water with agitation for 5 minutes can often help remove these residual particles. The quality of the etching was monitored via optical microscope and profilometer. The photoresist was removed using acetone and isopropyl alcohol. Photoresist residuals were then removed using $O_2$ plasma at 300 W for 5 minutes.

An insulator layer was then deposited on the microwire by OXFORD Plasma 80 Plasma-Enhanced Chemical Vapor Deposition (PECVD), which in this case was a 175 nm SiN layer as a diffusion barrier for the Cu and a 900 nm $SiO_2$ layer as an electrical and thermal insulation layer. A 100 nm SiN added on top for etching can reduce the roughness of the insulator layer. Deposition was performed at 300° C. The roughness of the insulator layer was measured using a profilometer. The 100 nm SiN layer was etched to reduce surface roughness by Reactive Ion Etching (REI) OSFORD Plasma 80 using $CF_4$ at 35 sccm and $O_2$ at 3.5 sccm for 1.9 minutes at 100 W. Surface roughness of the PECVD deposited layer can also be reduced by depositing at a lower temperature (e.g. 100° C.).

The resulting surface roughness was less than 10 nm. To further overcome the roughness after deposition of the insulator layer, a spin-on-glass (SOG) was applied. Specifically, the SOG layer was passed into a 0.2 mm filter on the wafer and spin coated at 3000 rpm for 1 minute. The wafer was then placed on a hotplate at 100° C. for 1 minute and then at 200° C. for 1 minute. This process can be repeated to increase the thickness of the SOG layer and further reduce the roughness of the wafer. The wafer was then placed in an oven under nitrogen atmosphere at 300° C. for 45 minutes.

Photolithography was again performed to open contact windows to the microwire. Specifically, a hexamethyldisilazane (HDMS)/xylene (20:80) adhesion promotor for the photoresist was deposited at 3000 rpm for 60 seconds. Photoresist 9620 was then deposited at 2000 rpm for 45 seconds and soft baked on a hotplate at 110° C. for 5 minutes and allowing to cool down for 20 minutes. The wafer was aligned with the mask and exposed to ultraviolet radiation for 60 seconds. Subsequently the wafer was dipped into a 1:3 AZ 400 developer to water for 1.5 minutes seconds.

The SOG, $SiO_2$, SiN, and Ti layers were etched on the windows to provide electrical contacts for the microwire. Specifically, RIE was performed using $CF_4$ at 50 sccm and $O_2$ at 5 sccm with 100 W forward power for 12 minutes. The etching temperature was 15° C. An 8 µm layer of photoresist was sufficient for masking. The photoresist was removed using acetone and isopropyl alcohol, followed by subsequent $O_2$ plasma treatment at 300 W for 5 minutes to remove photoresist residuals.

Photolithography was again performed to define the organic light emitting diodes (OLEDs). Specifically, a hexamethyldisilazane (HDMS)/xylene (20:80) adhesion promotor for the photoresist was deposited at 3000 rpm for 60 seconds. A positive photoresist 1813 was then deposited at 3000 rpm for 60 seconds and soft baked on a hotplate at 110° C. for 1 minute. The wafer was aligned with the mask and exposed to ultraviolet radiation for 20 seconds. Subsequently the wafer was dipped into a 1:1 AZ developer for 45 seconds, rinsed with deionized water, and dried under nitrogen.

The OLED backcontact electrodes were then deposited using denton sputting to form the following layers: a 10 nm Ti layer, an 80 nm Au layer, and a 3.5 nm Ti layer. The wafers were then soaked in acetone for a few minutes, then sonicated for 1.5 minutes, and immediately rinsed with isopropyl alcohol.

Photolithography was again performed to define the OLED active area. Specifically, a hexamethyldisilazane (HDMS)/xylene (20:80) adhesion promotor for the photoresist was deposited at 3000 rpm for 60 seconds. A positive photoresist 1813 was then deposited at 3000 rpm for 60 seconds and soft baked on a hotplate at 110° C. for 1 minute. The wafer was aligned with the mask and exposed to ultraviolet radiation for 20 seconds. Subsequently the wafer was dipped into a 1:1 AZ developer for 45 seconds, rinsed with deionized water, and dried under nitrogen. The wafers were then placed in the oven at 300° C. for 45 minutes. It is noted that an alternative approach to define the OLED active area can include depositing a 120 nm SiN layer via PECVD, and after photolithography, etch the SiN layer in the active area and the windows for electrical contacts.

O$_2$ plasma was then used to oxidize the Ti layer to change the work function of Ti and use the hydrophilic property of TiO$_2$ for deposition PEDOT:PSS for the OLED structure. The wafer was covered with photoresist 1813 before dicing to keep the active area clean. A programmable silicon dicing saw (Disco DAD641) was used to dice the wafer with a 250 mm dicing blade. The photoresist was removed using acetone and isopropyl alcohol, as described previously. The active area of the device was exposed to a UV Ozone Cleaner under O$_2$ atmosphere for 7 minutes.

PEDOT:PSS was then coated on the structure and subsequently dried on a hotplate at 110° C. for 10 minutes. SY-PPV was then coated and dried on a hotplate at 100° C. for 5 minutes. A 7 nm Ca layer and 150 nm Al layer were deposited via a glove box evaporator. An encapsulating epoxy layer was then coated and cured at ambient temperature for 12 hours.

Example 2—Fabrication of Another Spintronic Device

The layer stack developed for the experiments presented in this study resulted from the requirement to stack organic thin-film devices directly on top of highly conducting RF thin-film wires that can be operated at room temperature, provide good electrical insulation and thermal isolation to the organic device layers as well as a smooth interface with a roughness below 10 nm, while, at the same time, provide good heat sinking. To meet all these requirements at the same time is technologically non-trivial.

Bulk Cu is an excellent room-temperature conductor, but the surface of a layer stack consisting of Cu films with a thickness on the order of a micron and subsequently deposited, equally thick insulating layers is too rough and thus, unsuitable for the deposition of thin-film organic semiconductor devices. Thus, in order to smooth out the surface roughness and to allow fabrication of organic electronic devices on top of the Cu microwire, a spin-on-glass (SOG) intermediate coating (IC1-200) was used, provided by Futurrex, Inc., which is a polysiloxane-based spin-on dielectric material. In this geometry, a dielectric materials stack provides all the heat isolation, electrical insulation and the mechanical smoothing functions which are needed.

The layer stack, as illustrated in FIGS. 3A-3B, constitutes a system of successfully deposited thin-film materials, with intermediate lateral structuring steps which together created a thin-film wire system with the numerous beneficial properties: The application of AC currents in the radio-frequency to microwave-frequency range allowed for the generation of very homogeneous, high-amplitude in-plane AC magnetic fields which were utilized for magnetic resonance application. The thin film wire was electrically insulated and thermally isolated from the surface of the stack system. Heating of the wire during continuous operation changed only marginally the stack surface as the heat was drained through the silicon substrate below the layer stack. The surface of the layer stack had very low roughness (few nm range) allowing for the deposition of the thin-film layers, i.e. the organic semiconductor layer stacks for bipolar injection device used in the experiments presented in Example 3.

In order to implement the stack system, the following layer stack was used:
Silicon substrate
Optional 50 nm SiO$_2$ layer for substrate adhesion
200 nm SiN for electrical insulation and diffusion barrier for the Cu but not too strong thermal isolation from substrate
70 nm Ti for adhesion
1µ Cu for the thin-film wire
10 nm Ti for adhesion
5 nm Au as etch stop for lateral structuring
8 nm Ti for adhesion
175 nm SiN
930 nm SiO$_2$ for electrical and thermal insulation
340 nm Spin-on-glass (930 nm) in order to reduce roughness
10 nm Ti for adhesion
80 nm Au as back contact for the organic layer stack with appropriate work function for hole injection. Although Au can be suitable, Ag or other conductive materials can also be suitable.
3 nm Ti for adhesion—due to the very small thickness, the surface work function was determined by the underlying Au layer. The Au layer can be optionally surface modified to adhere to PEDOT OLED layers.

A Heidelberg MicroPG 101 Pattern Generator was used to form the layers and patterns. The mask was developed with developer AZ 1:1 for 45 sec. Mask cleaning took place using spin rinse dryers (SRD). The mask design pattern and sizes were verified by optical microscopy. The mask was placed in a chrome etch for 2.5 min, cleaned in DI water for 2 min, and then cleaned in a SRD. A low stress 200 nm SiN film at 800° C. was deposited on (100) surface oriented c-Si wafers wafers using Low Pressure Chemical Vapor Deposition (LPCVD). The thickness of SiN was verified using a NANOSPEC reflectometer.

The following layers were deposited via sputtering using a 3 mTorr Argon plasma:
Ti 20 nm (adhesion/diffusion barrier)
Cu 1 um (microwire)
Ti 5 nm (adhesion)
Au 6.5 nm (etch stopper/electrical contact)
Ti 8 nm (adhesion for next layer)

Photolithography for the definition of the microwire used HMDS/Xylene (20:80) at 3000 rpm for 60 sec to improve adhesion of photoresist to surface. A positive photoresist 1813 was deposited at 3000 rpm for 60 sec followed by soft bake using a hotplate at 110° C. for 1 min. The wafer was aligned with the lithography mask and exposed to UV light for 20 sec. The assembly was dipped into developer Az 1:1 for 45 sec and then rinsed in DI water, followed by drying with N$_2$. The assembly was then post baked on a hotplate at 110° C. for 2 min.

Structuring of the microwire used a wet etch conducted at a wet bench. After each step the wafer was thoroughly rinsed with DI water. Residual particles that were stuck to the surface, especially around the edges of microwire were flashed off the wafer with a DI water spray. Similarly, immersing the wafer in DI water container with agitation for 5 min helped to remove residual particles. The etch quality was checked using an optical microscope and a profilometer. Removal of the photoresist took place by employment of acetone and isopropanol (IPA), electronic grade. For the removal of photoresist residuals, an O$_2$ plasma was used.

Example 3—Evaluation of a Spintronic Device

Figure 4A:
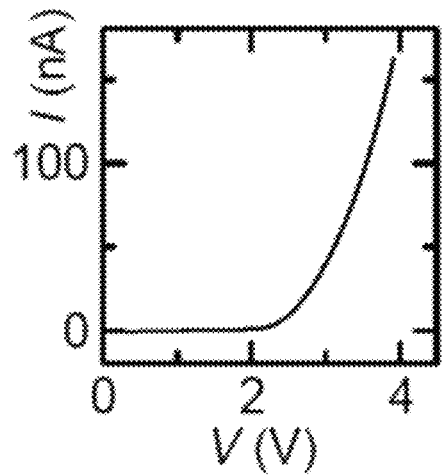
FIG. 4A is a graph of current-voltage characteristics of a spintronic device, in accordance with examples of the present disclosure.
Figure 4B:
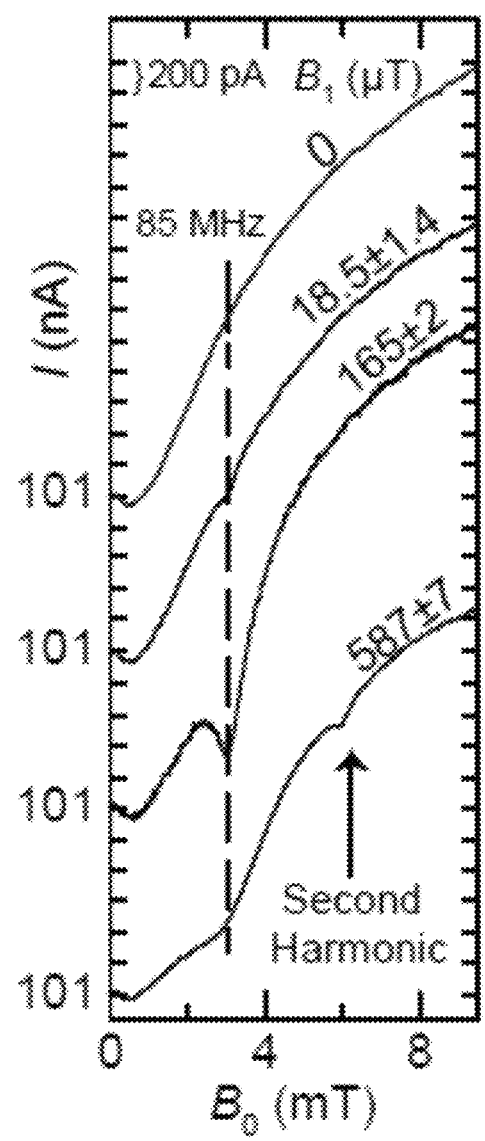
FIG. 4B is a graph of magnetoconductivity characteristics with no RF field (top), and with RF fields of different amplitudes. At the highest driving fields, a second-harmonic feature appears in the resonance spectrum due to the nonlinearity of the RF source, and is of no further relevance.

A spintronic device manufactured according to Example 2 was further characterized. FIG. 4A shows a current-voltage characteristic of the device. The OLED current shows the expected diode characteristics, turning on just above a bias of 2 V. At constant voltage, the current of the device changes under application of an external magnetic field B$_0$. The top curve in FIG. 4B shows the magnetoconductivity characteristics of a device operating at a current of 101 nA. Note that the tick marks correspond to a current change of 200 pA. The current initially decreases slightly with increasing $B_0$ within the first 0.2 mT from the origin (the ultrasmall magnetic field effect) and subsequently increases again. The lower three curves show the same measurements, offset on the current axis, with oscillating $B_1$ fields applied at a frequency of 85 MHz and amplitudes of 18.5±1.4, 165±2 and 587±7 µT, respectively. The RF field leads to a dip in the magnetoconductivity curves. This dip results from the fact that hyperfine fields induce mixing between singlet and triplet electron-hole pair states in the conjugated polymer, and the external magnetic field $B_0$ tends to suppress this mixing. The external RF field reopens the mixing channel at the resonant magnetic field, quenching the current. As $B_1$ increases from 18.5 to 165 µT, the resonance deepens but also broadens. This effect is a consequence of power broadening, arising from the fact that the large $B_1$ amplitude results in a larger number of individual spins within the hyperfine-broadened ensemble coupling to the oscillatory field. At 587 µT, the resonance spectrum is clearly broadened, but the amplitude is also decreased. This reduction in the resonance amplitude is a signature of the emergence of ultrastrong coupling, which leads to the formation of a new spin basis set and new transition selection rules. We note that, in addition to the spin-½ resonance at 3.07 mT (85 MHz), at the highest driving fields a second-harmonic feature is also observed in the current at 6.14 mT. This second harmonic likely arises from the slight non-linearity of the RF amplifier, which will lead to a weak second-harmonic component in the RF radiation generated in the stripline at the nominal frequency of 85 MHz. We stress that all measurements are of the steady-state current, without the need for modulation or lock-in detection. It is not possible to achieve sufficient RF power in the OLED in non-monolithic devices to enable direct-current detection.

Figure 4C:
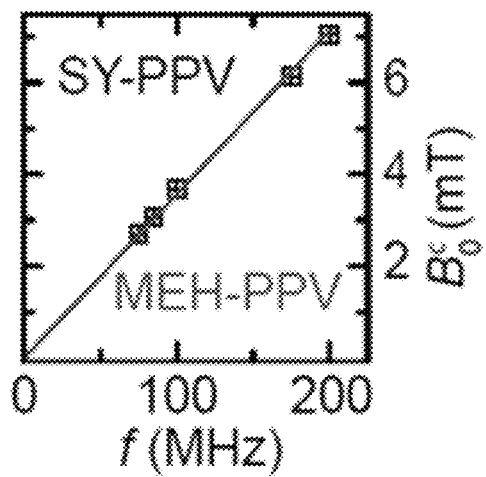
FIG. 4C is a graph of the linear relation between the peak of the resonance spectrum $B_0^c$ and the driving frequency, compared to the relation extracted at very low fields for the related polymer material MEH-PPV.

The resonance feature follows the dependence of position of the resonance peak $B_0^c$ on driving frequency f expected for a free electron, as plotted in FIG. 4C. The regression line shows the relationship extracted in the low-$B_1$ regime for a related polymer material, poly[2-methoxy-5-(2-ethylhexyloxy)-1,4-phenylenevinylene] (MEH-PPV). To demonstrate the quality of the data, the differential current recorded on resonance at $B_1$=52(1) µT is plotted in FIG. 4D. The spectrum is accurately described by the sum of two Gaussian functions (the largest peak), with the two Gaussians (middle peak and small broad peak). The two Gaussians arise from the hyperfine-field distributions experienced by the electron and hole wave-functions in the polymer, respectively.

Figure 4D:
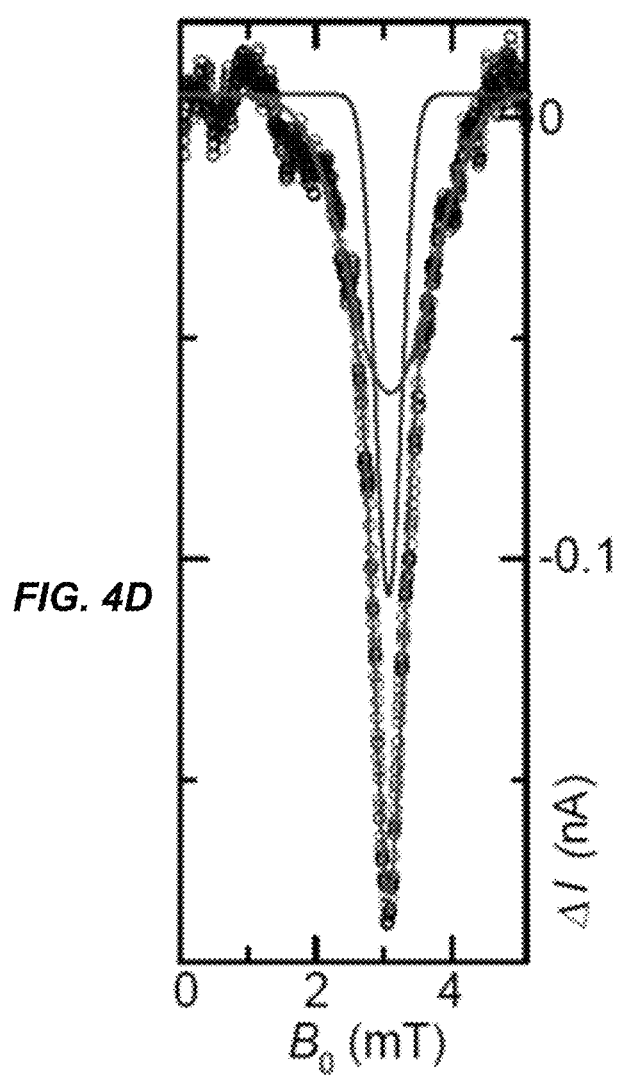
FIG. 4D is a graph of the low-field magnetic resonance spectrum extracted from the difference between the zero-field and the finite-field magnetoconductivity curves. The spectrum is accurately described by the sum (largest peak) of two Gaussian functions (middle peak, short broad peak) originating from the two hyperfine field distributions experienced by the electron and hole spins, respectively.
Figure 5:
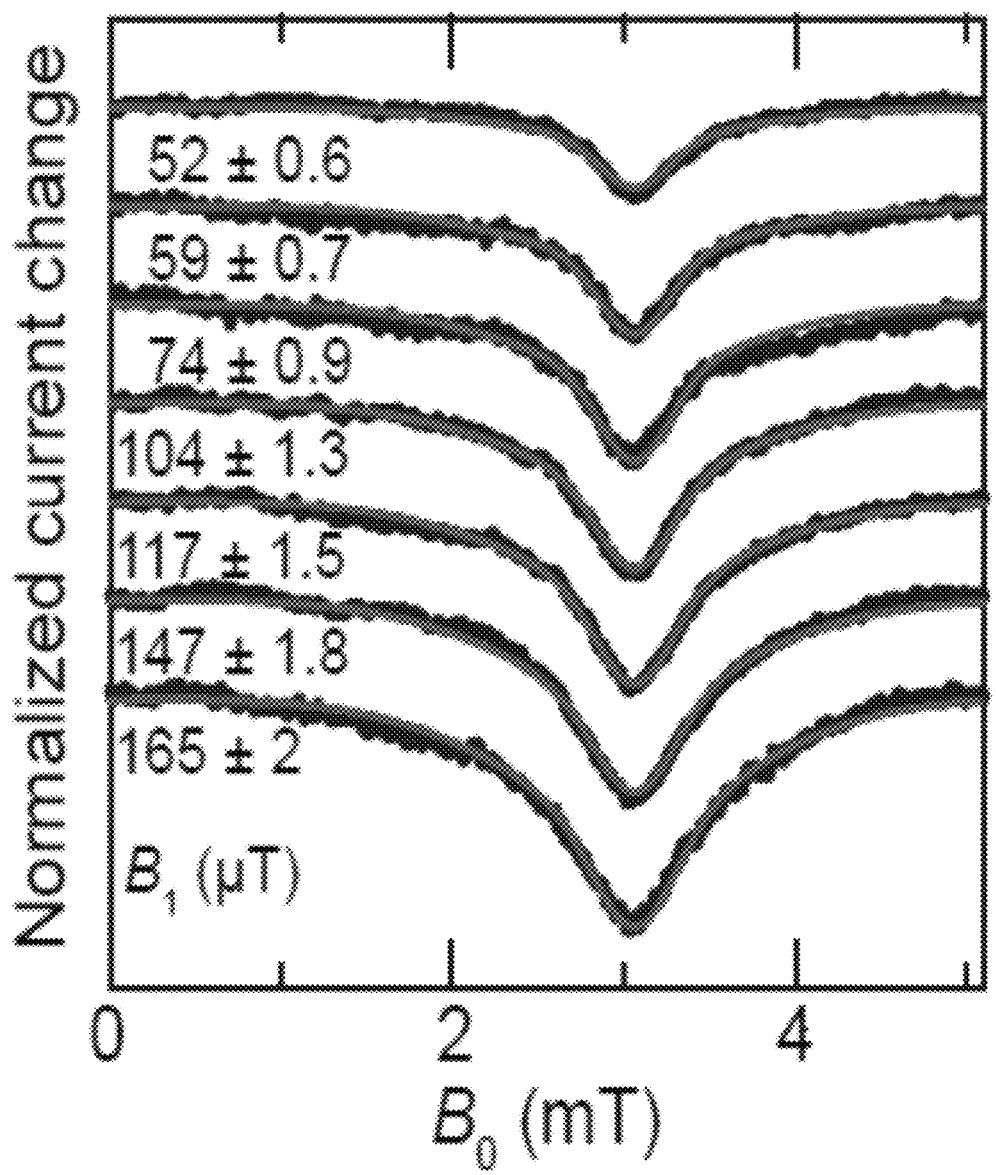
FIG. 5 is a graph of spectra that are described by a convolution of the two Gaussian curves shown in FIG. 4D and a Lorentzian function arising from power broadening. A global fit is used to extract the $B_1$ strength.

In examining the dependence of resonance spectrum on $B_1$ strength, one of the biggest challenges lies in accurately determining the magnitude of $B_1$. This parameter can neither be measured directly with an external detector, since the RF stripline does not radiate—the resonance effect is generated in the near-field of the stripline; nor can it be calculated accurately, since the stripline invariably suffers from reflection and coupling losses and the local field is highly inhomogeneous. In time-resolved electrically detected magnetic resonance experiments, $B_1$ can be determined from the Rabi precession frequency. Here, the effect of power broadening on the resonance spectrum is examined to determine the magnitude of $B_1$. Power broadening gives the spectrum the shape of a Lorentzian curve, whereas the underlying statistical distribution of local hyperfine fields experienced by each spin follows a Gaussian shape, with each carrier species being described by a distinct Gaussian curve. At low driving powers, the hyperfine disorder dominates the spectrum so that a pure double-Gaussian shape emerges as shown in FIG. 4D. As the power increases, the spectral shape changes gradually from double-Gaussian to Lorentzian, with intermediate fields showing a spectrum consisting of a convolution of the two, a double-Voigt line. FIG. 5 shows examples of resonance spectra recorded at different RF excitation powers, with the power increasing from top to bottom. The spectra clearly broaden with increasing power. Using a global fitting procedure for all data with only the two hyperfine distributions of electron and hole spin along with $B_1$ as the three fitting parameters for all data sets, a precise value of $B_1$ can be assigned to each resonance spectrum.

The fitting procedure was performed as follows. In the low radio frequency (RF) driving power regime, the electron spin resonance linewidth of charge carriers in organic semiconductors are well described by two Gaussian functions with equal centers at a Landé-factor at g~2.023, whose different widths correspond to the distributions of proton induced hyperfine fields experienced by electron polarons and hole polarons, respectively. As the driving power increases the effect of power broadening, the electrically detected magntic resonance (EDMR) lines eventually both assumed a Lorentzian shape governed by the strength of the driving field $B_1$ (the full width at half maximum will be equal $2B_1$). In the intermediate power regime, when both power broadening and the inhomogeneity caused by the hyperfine fields are significant a convolution of a Gaussian and a Lorentzian function, the so called Voigt function described the polaron resonances appropriately.

For the fit of the polaron pair EDMR lines presented here, double Voigt functions $$y = A \frac{2\ln(2)}{\pi^{3/2}} \frac{w_L}{w_{G1}^2} \int_{-\infty}^{\infty} \frac{e^{-t^2}}{\left(\sqrt{\ln 2}\, \frac{w_L}{w_{G1}}\right)^2 + \left(\sqrt{4\ln(2)}\, \frac{x - x_{c1}}{w_{G1}} - t\right)^2} dt +$$

$$\frac{R}{} \frac{2\ln(2)}{\pi^{3/2}} \frac{w_L}{w_{G2}^2} \int_{-\infty}^{\infty} \frac{e^{-t^2}}{\left(\sqrt{\ln 2}\, \frac{w_L}{w_{G2}}\right)^2 + \left(\sqrt{4\ln(2)}\, \frac{x - x_{c2}}{w_{G2}} - t\right)^2} dt$$

were used. Here, $x_{c1}$ and $x_{c22}$ are the centers of the resonance lines and R is the ratio between the resonance line intensities A of the first resonance line and A/R of the second resonance line. The Gaussian widths of the two Voigt functions are $w_{G1}$, $w_{G2}$, respectively, while only one common Lorentzian $w_L$ is needed since power broadening is identical for all paramagnetic centers that are exposed to the same radiation field. Since $w_L = c\sqrt{p}$, where p is the RF power applied by the thin film wire and $2B_1 = w_L$. The error in $B_1$ is determined by the error of the conversion factor c, that resulted from the fit procedure.

Given the large number of fit parameters in the EDMR fit function provided above, the line width was measured repeatedly for various applied RF powers. The resulting data sets, as shown in the FIG. 5, were fit globally, i.e. the function given above was applied simultaneously to all obtained data sets while only the power variable p was changed.

Figure 6A:
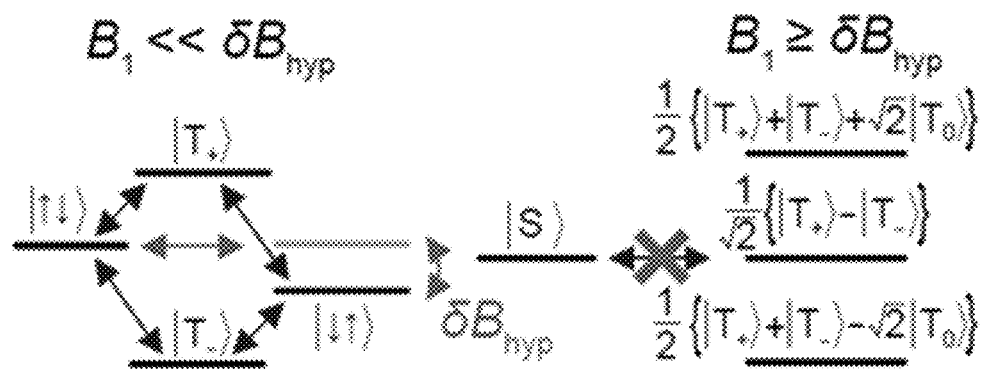
FIG. 6A depicts a change of the spin basis set probed in magnetic resonant transitions from the low $B_1$ field regime to the onset of the regime of the spin-Dicke effect at high resonant driving fields.
Figure 6B:
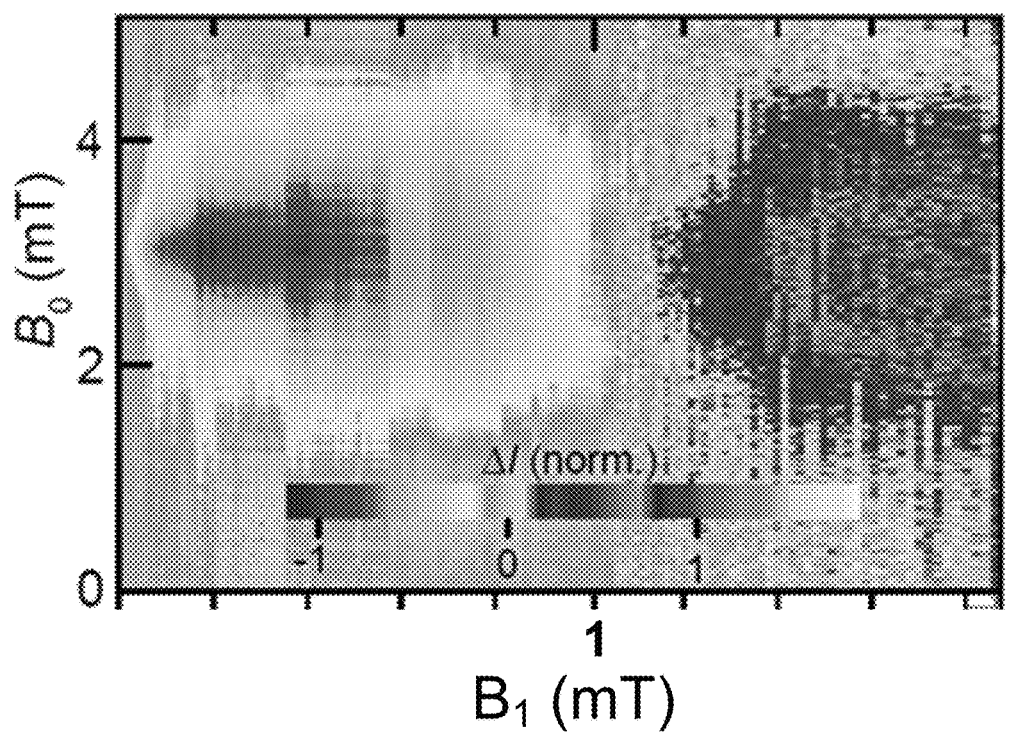
FIG. 6B depicts raw data of magnetoconductivity curves as a function of driving power at 85 MHz, plotted on a false color scale, showing power broadening of the resonance, bleaching and a subsequent inversion of resonance sign at high driving fields.
Figure 6C:
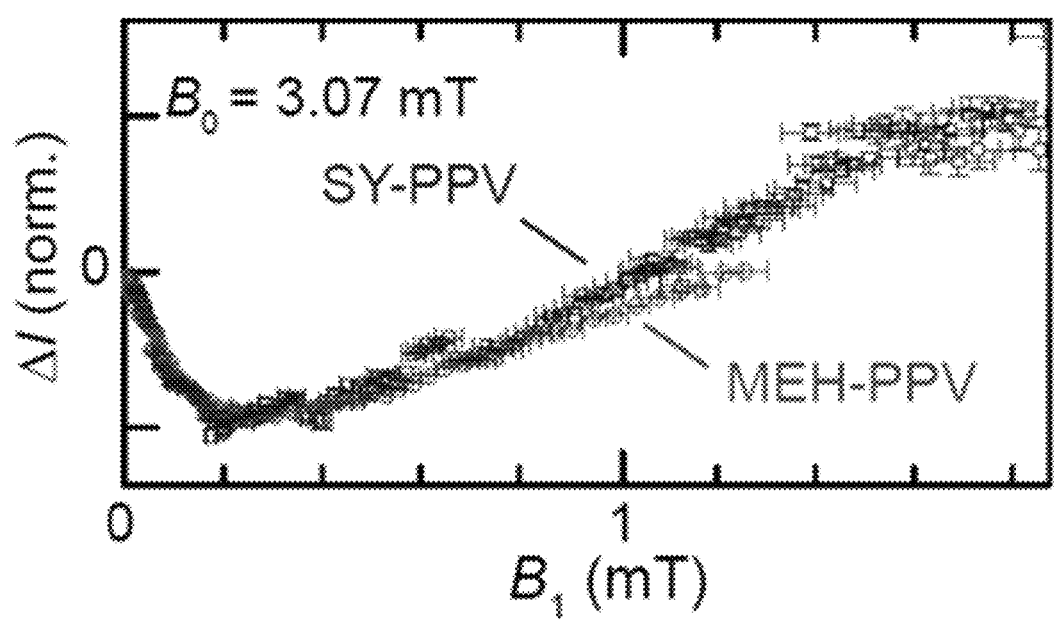
FIG. 6C is a plot of the amplitude of the resonance maximum at 3.07 mT as a function of $B_1$ compared to results obtained with a different conjugated polymer material, MEH-PPV, in an OLED driven by a coil rather than a stripline.

With accurate values of $B_1$ extracted for a given power, the effect of driving field strength on the resonance spectrum was investigated. The spin states responsible for magnetic resonance change as the driving field is raised from the weak-coupling low-field (perturbative) to the ultrastrong-coupling high-field regime. FIG. 6A summarizes the two limits. In the perturbative regime, the driving field $B_1$ is much smaller than the average difference in the distribution of hyperfine fields experienced by the two charge carriers, $\delta B_{hyp}$. This field lifts the degeneracy between the antisymmetric pair states of triplet and singlet symmetry, $T_0$ and $S_0$. Magnetic resonance transitions then occur to the pure triplet states $T_+$ and $T_-$. In contrast, when $B_1$ is of the order of or larger than $\delta B_{hyp}$, the approximation of pure single-spin states breaks down. Three new triplet superposition states emerge as stated in FIG. 6A, besides the pure singlet state. However, the selection rules for allowed magnetic resonance transitions change. Transitions between singlet and triplet are blocked and only occur between the three new superposition triplet levels. This change of basis set is a consequence of indistinguishability of the spin pair with respect to the driving electromagnetic field: once the driving field strength exceeds inhomogeneous broadening, which arises predominantly from the local hyperfine fields, the individual spins of the pairs become quantum mechanically indistinguishable, necessitating a description in terms of a new common wavefunction. This phenomenon is a manifestation of the Dicke effect, which is best known from superradiant luminescence of atomic gases, and has a profound effect on the magnetic resonance amplitude and spectrum. FIG. 6B plots the normalized device current change $\Delta I$ as a function of $B_0$ and $B_1$ on a false-color scale. The maximal resonance amplitude is shown in FIG. 6C. Initially, the overall amplitude, which is negative since it measures current quenching, rises with increasing $B_1$ but then saturates around $B_1=0.2$ mT. Subsequently, the resonance amplitude decreases again, until the resonance vanishes completely at $B_1=1.1$ mT. Subsequently, the resonance inverts and shows the same effect of power broadening as seen for very low $B_1$ fields, but with reversed sign.

Previous exploration of this exotic regime of magnetic resonance was probed in a similar conjugated polymer, MEH-PPV, with devices mounted in an external RF coil to generate the high $B_1$ fields. This approach requires very high driving powers for the coils and leads to heating of the device and, ultimately, catastrophic breakdown: the coils simply evaporate and the OLED overheats. Notably, for $B_1$ fields generated with coils around devices of MEH-PPV, which has a comparable hyperfine coupling strength to SY-PPV, the inversion of the resonance sign was not demonstrated to signify the emergence of the Dicke regime. This transition is now clearly resolved in the new data in FIGS. 6A-6C. Nevertheless, up to a field of $B_1=1.2$ mT, the MEH-PPV data closely follow those acquired here for SY-PPV. The comparison between the two measurements is important, since it demonstrates the accuracy of the $B_1$ calibration carried out here. The coils used in the earlier experiment could be pulsed, so that Rabi oscillations could be measured directly in the time domain, providing an absolute measure of $B_1$. Finally, it is noted that the measurement technique is highly sensitive to potential heating effects arising from the stripline, since these would lead to a change of the current-voltage characteristic, which is recorded for every $B_1$ field. There does not appear to be any change of the I-V characteristics with $B_1$ off resonance, implying that, in the field range studied here, heating effects can be neglected.

Example 4

This example illustrates fabrication of monolithic copper-based lithographically defined wires for broadband (low-Q) EPR excitation located 1 micron beneath organic light emitting diode (OLED) stacks with a circular surface area of 57 μm diameter that will allow for high $B_1$ and low $B_0$ EDMR spectroscopy. For the fabrication of these integrated resonator/OLED devices, we deposited crossed wires on top of a quartz substrate, followed by the deposition of a 1 micron thick dielectric insulator stack below an OLED back contact. These template structures where brought into an inert glovebox environment where the OLED device layers were deposited.

Figure 7:
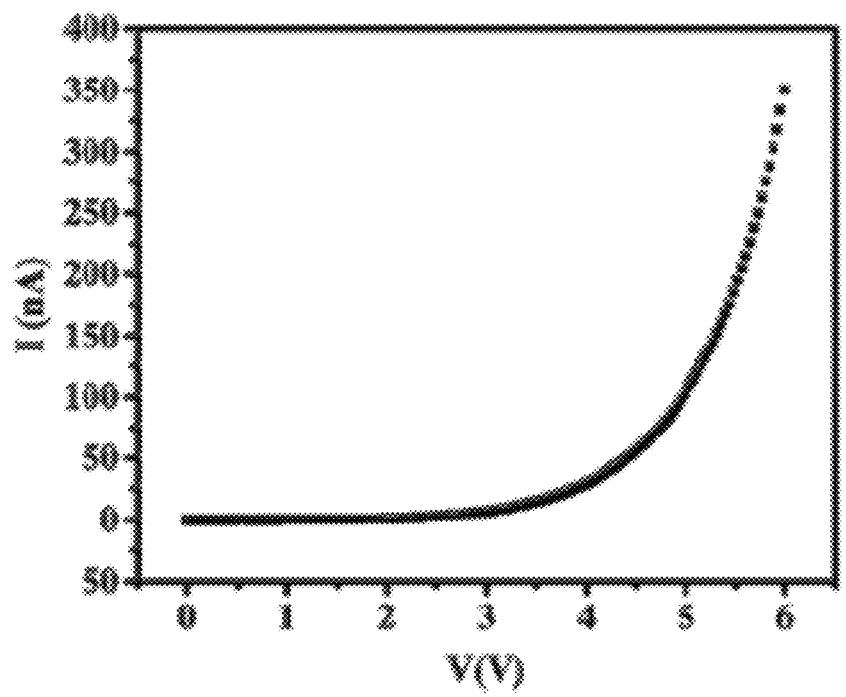
FIG. 7 is a plot of current as a function of voltage for an example spintronic device.

A monolithic spintronic device was fabricated similar to Example 2. In this example, the starting substrate was quartz instead of Si/SiN (FIG. 1). 1 μm thick copper wires were fabricated to induce a $B_1$ field underneath OLED back contact Ti/Ag/Ti layers. Layers of SiN, $SiO_2$ and spin-on-glass (SOG) with a total thickness of more than 1 μm were used as insulation. FIG. 7 is graph of current as a function of voltage for the formed device.

Figure 8A:
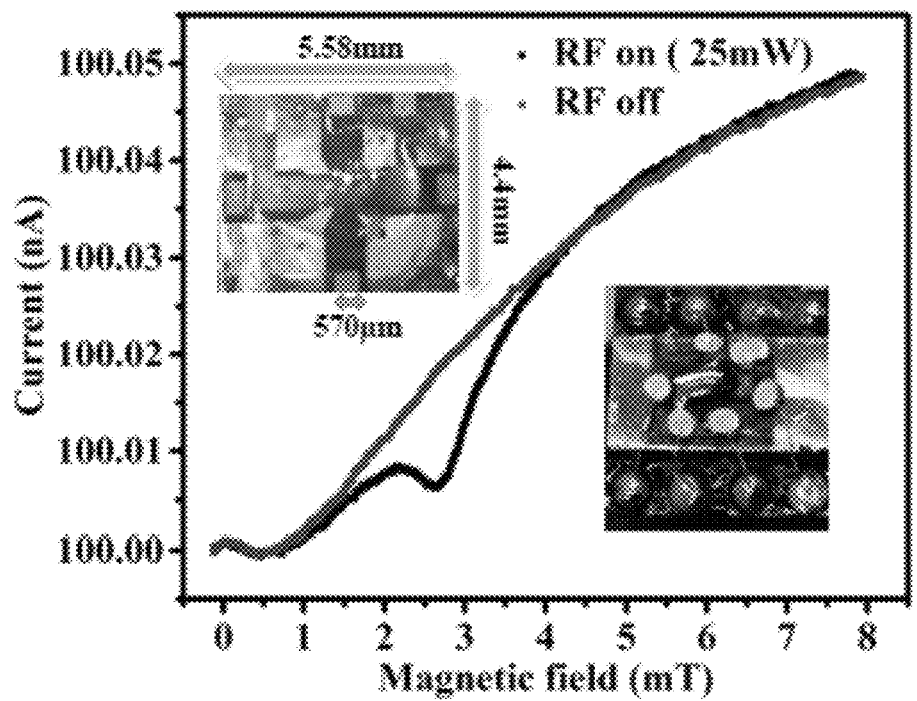
FIG. 8A is a magnetoresistance graph of current as a function of swept magnetic field $B_0$.
Figure 8B:
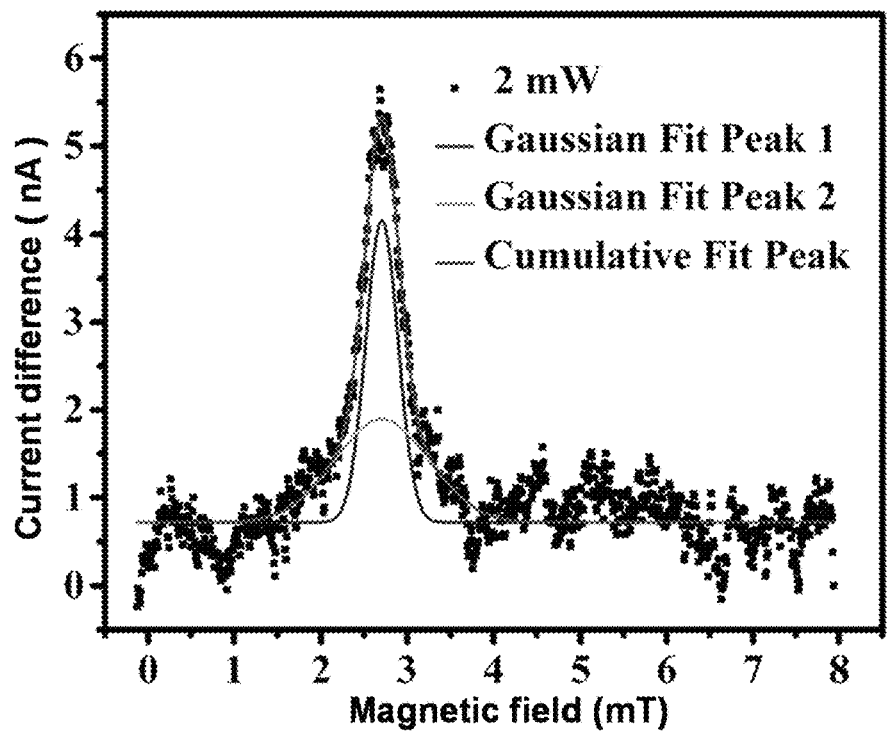
FIG. 8B is a magnetoresistance graph of current difference as a function of swept magnetic field $B_0$.
Figure 8C:
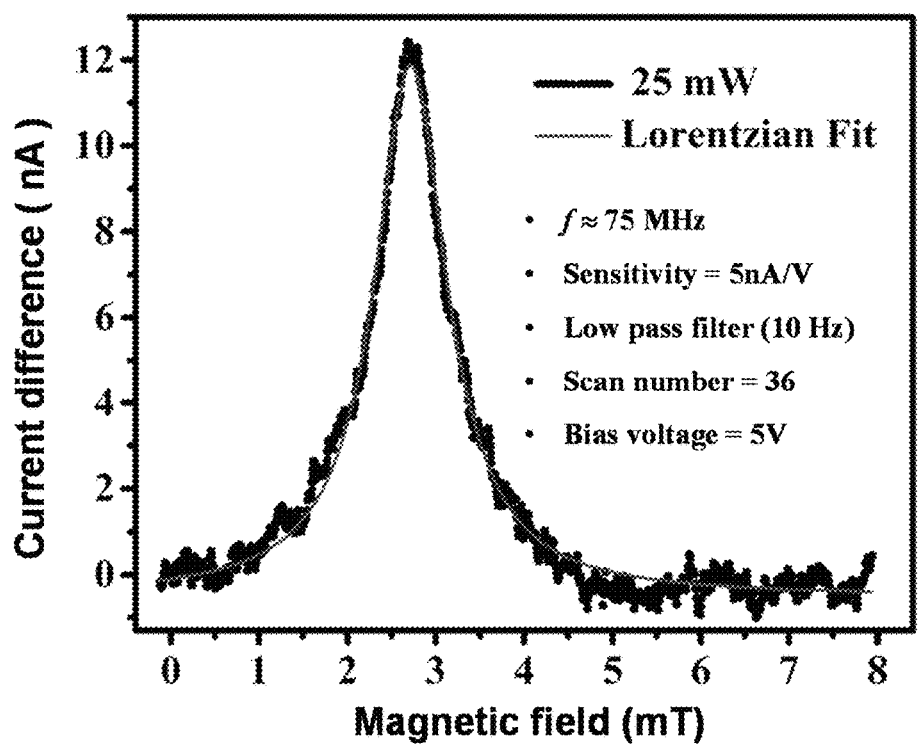
FIG. 8C is a magnetoresistance graph of current difference as a function of swept magnetic field $B_0$.
Figure 8D:
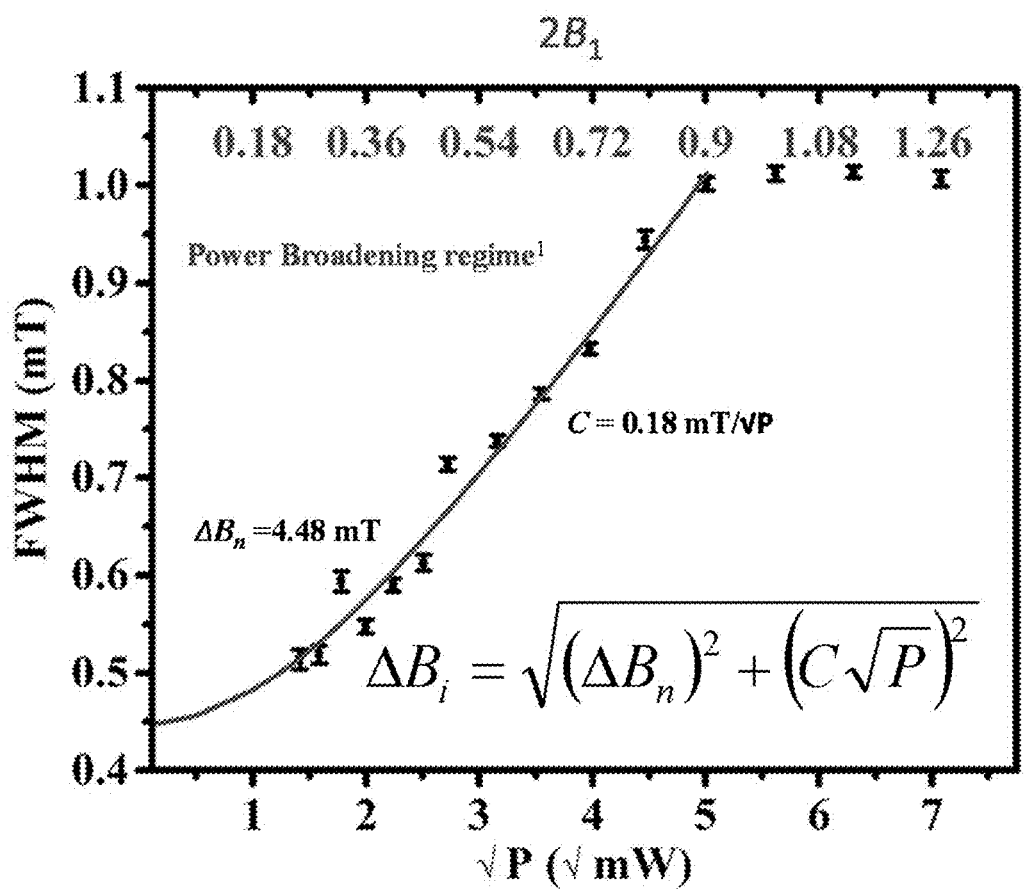
FIG. 8D is a graph of inhomogeneously power-broadened MR line width at various power levels which was used to determine magnetic field $B_1$.

DC magnetoresistance in the OLED was measured by detecting changes in device current while sweeping the magnetic field $B_0$ as reported in FIG. 8A-8C. Magnetic resonance (MR) was induced by applying RF field to microwire. In order to determine $B_1$, we measured the inhomogenously power-broadened magnetic resonance line width $\Delta Bi$ for various RF powers P, and determined the natural line width $\Delta Bn$ and the conversion factor C numerically as shown in FIG. 8D.

The integrated devices allow for EDMR spectroscopy over broad frequency ranges with high driving field $B_1$ to square-root-of-power ratios as well as thin film induced magnetic field modulation. In the RF range (f~100 MHz) the structures allow for the continuous-wave application of $B_1>1$ mT without any recognizable heating effect and without the use of RF amplifiers (<50 mW produce $B_1>1.2$ mT). These structures can be used not just for magnetometry but also for non-linear EDMR spectroscopy at high B1 and low frequency/$B_0$ conditions.

Example 5

Figure 9A:
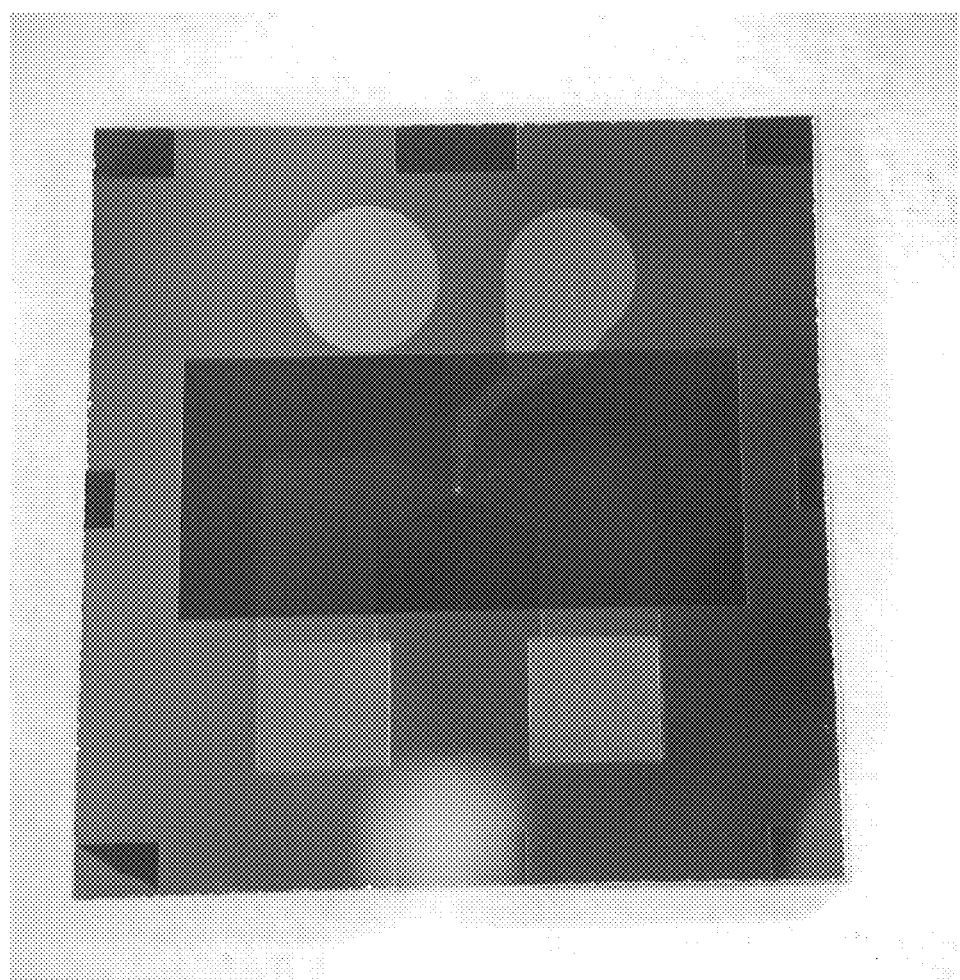
FIG. 9A is a schematic of a magnetometer configuration in accordance with one example.

A monolithic spintronic device was formed in a similar manner to Examples 2 and 4, with the configuration shown in FIG. 9A to operate as a magnetometer, including the 50 nm $SiO_2$ layer as an adhesion layer which has insulating properties. In this configuration the thin film wire is formed on the silicon substrate in a U-shape. This allows contact pads to be oriented on a common side of the device. Similarly, the thin-film device was formed in the active area and having a larger exposed contact pad. This configuration can be particularly useful for very high excitation power. The positions of RF contacts and sample contacts are well separated to avoid possible cross-talk between the wires that connects to these contacts. The shape of the wires can also be varied as desired and this design is one possible example.

Figure 9B:
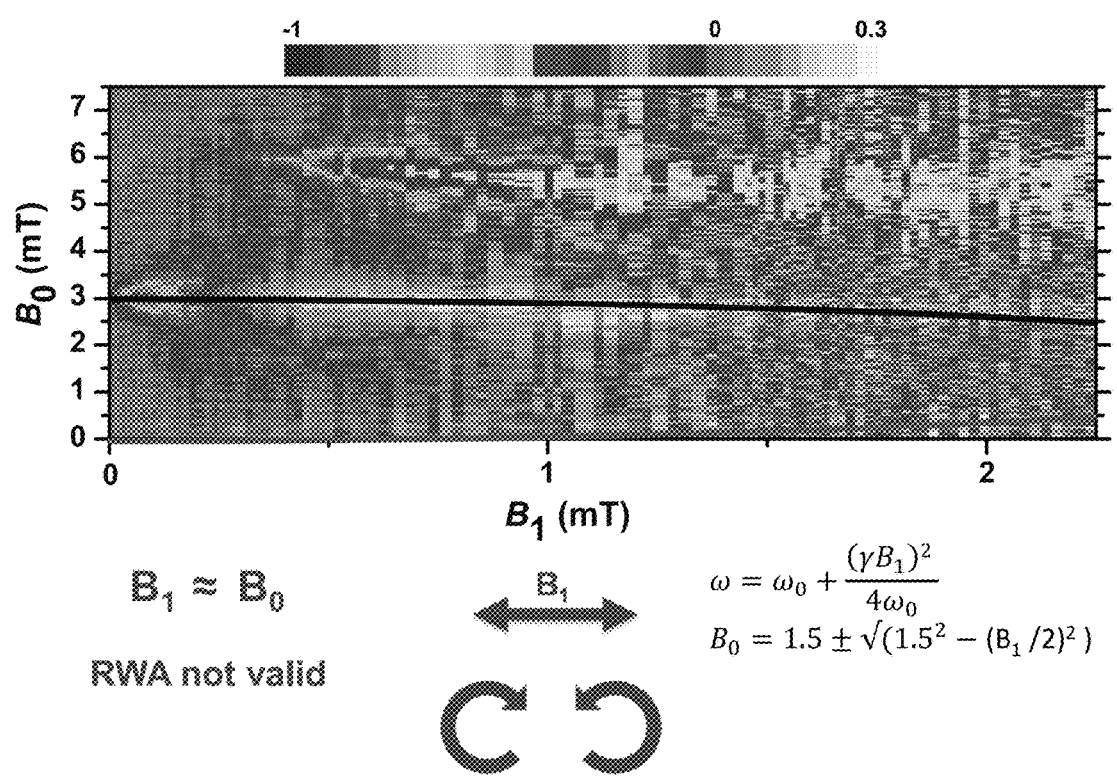
FIG. 9B is a plot of observed Bloch Siegert shift using the configuration of FIG. 9A. This plot is of raw data of magnetoconductivity curves as a function of driving power at 85 MHz, plotted on a false color scale, showing power broadening of the resonance, bleaching and a subsequent inversion of resonance sign at high driving fields, as well as clearly showing a Block Siegert shift which has not been previously experimentally observed.

FIG. 9B shows observed Bloch Siegert shift in this configuration where the organic semiconductor material is a fully deuterated MEH-PPV, with much lower hyperfine that results in narrow resonance line width which also results in increasing the sensitivity of the magnetometer. This plot is of raw data of magnetoconductivity curves as a function of driving power at 85 MHz, plotted on a false color scale, showing power broadening of the resonance, bleaching and a subsequent inversion of resonance sign at high driving fields. Furthermore, this plot clearly shows a Block Siegert shift (black line and lower red line) which has not been previously experimentally observed.

Figure 9C:
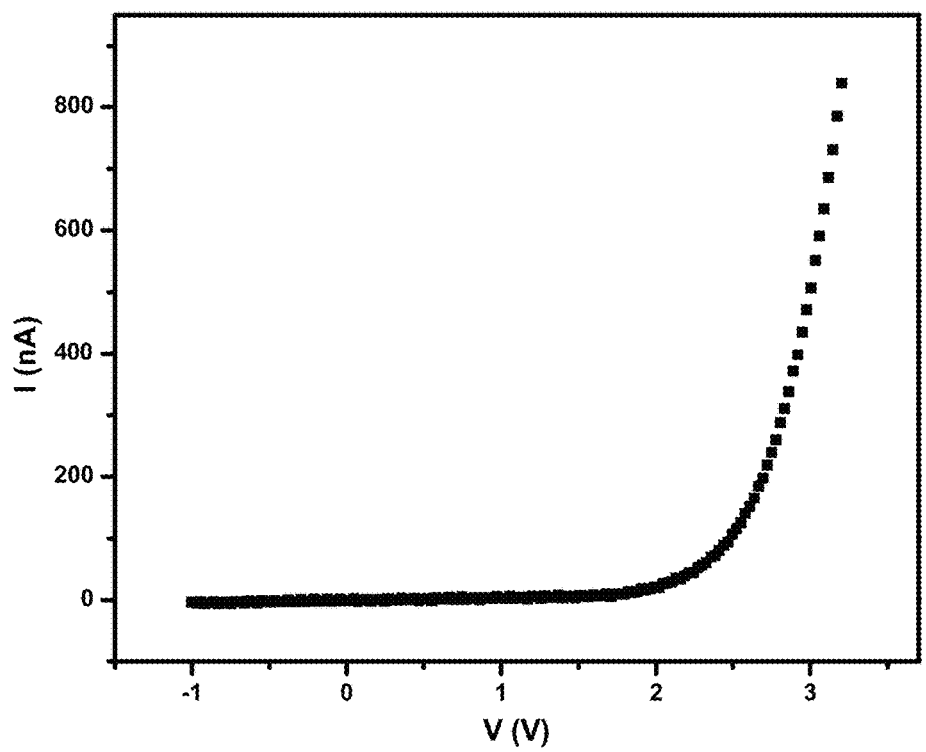
FIG. 9C is a plot of current as a function of voltage for the example of FIG. 9A.

FIG. 9C is a plot of current as a function of voltage for the example of FIG. 9A.

Figure 9D:
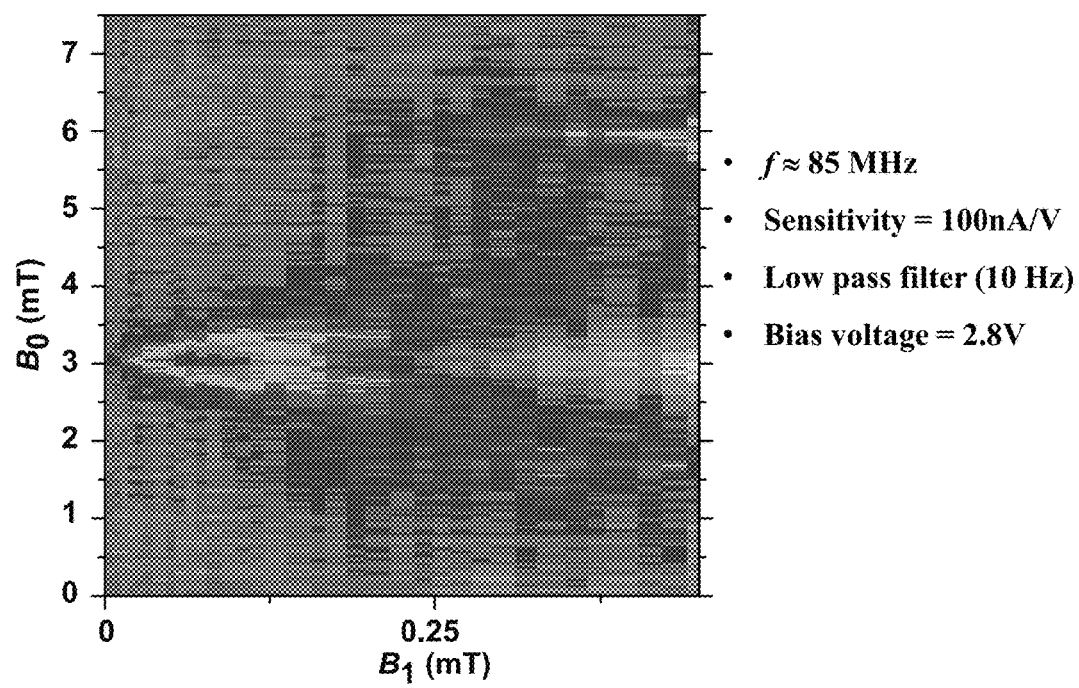
FIG. 9D is a plot of raw data similar to FIG. 9B for the example of FIG. 9A.

FIG. 9D is a plot of raw data from a magnified portion of FIG. 9B.

Figure 9E:
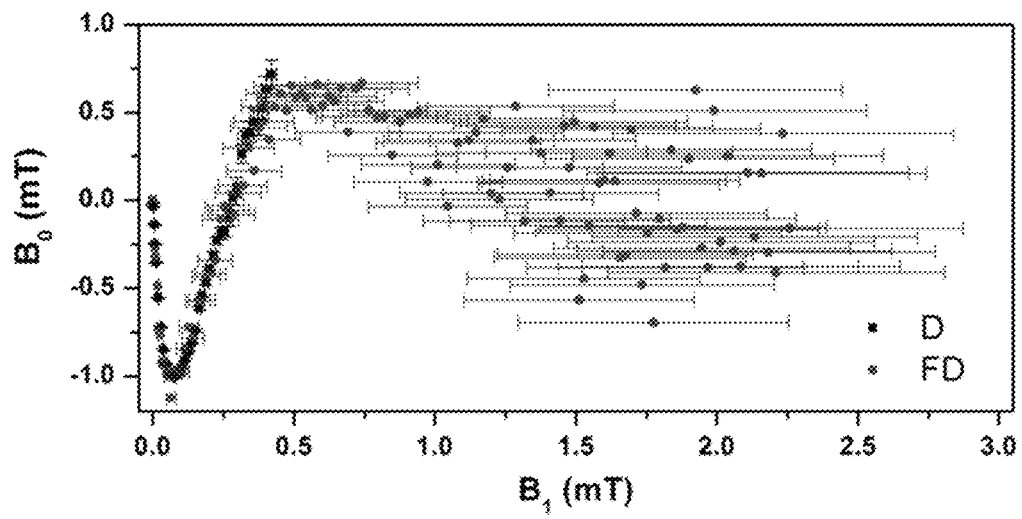
FIG. 9E is a plot of the amplitude of the resonance maximum at 3.07 mT as a function of $B_1$ compared to results obtained with a different conjugated polymer material, MEH-PPV, in an OLED driven by a coil rather than a stripline for the example of FIG. 9A.

FIG. 9E is a plot of the amplitude of the resonance maximum at 3.07 mT as a function of $B_1$ compared to results obtained with a different conjugated polymer material, MEH-PPV, in an OLED driven by a coil rather than a stripline for the example of FIG. 9A. Notably, the scale for deuterated (black) is 2.5 times that shown in the y-axis labels which is scaled for the fully deuterated (FD) data. This also illustrates that hyperfine field for fully deuterated based devices are 2.5 times lower than deuterated devices.

Figure 9F:
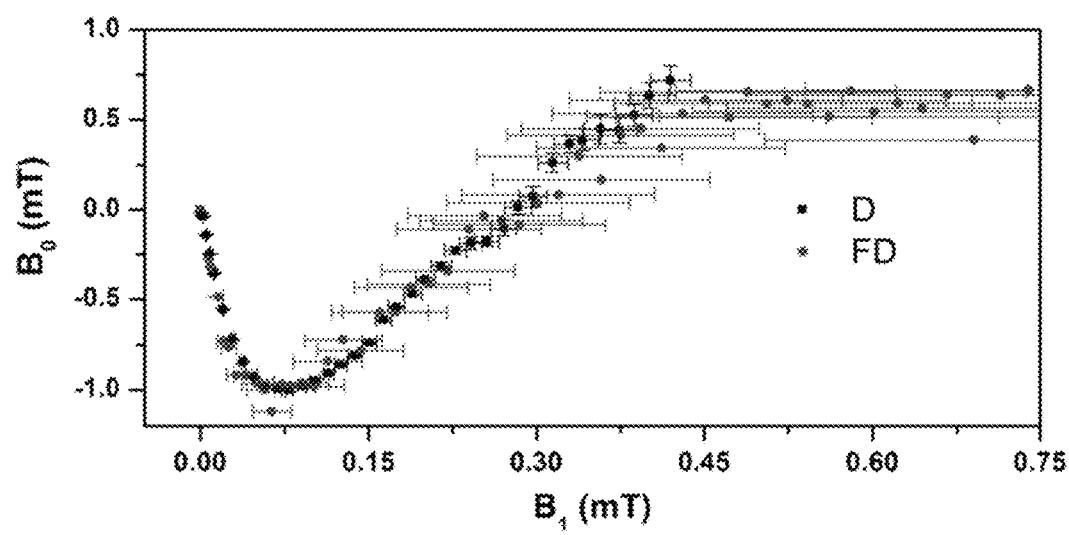
FIG. 9F is an exploded view of a portion of data from FIG. 9E.

FIG. 9F is an exploded view of a portion of data from FIG. 9E.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

What is claimed is:

1. A monolithic reusable microwire assembly, comprising:
    a substrate;
    an electrically conductive thin-film wire formed on the substrate, said thin film wire having a narrow segment forming an active area;
    a thermally and electrically insulating barrier formed on the electrically conductive thin-film wire;
    a roughness-reducing layer formed on the thermally and electrically insulating barrier, said roughness-reducing layer having a surface roughness of less than or equal to 20 nm; and
    a substrate adhesion layer, a thin film wire adhesion layer, a diffusion barrier layer, or a combination thereof formed between the substrate and the thin film wire.

2. The monolithic reusable microwire assembly of claim 1, wherein the substrate comprises silicon, quartz, glass, plastic, or a combination thereof.

3. The monolithic reusable microwire assembly of claim 1, wherein the substrate is not thermally isolated from the thin film wire and functions as a heat drain for the thin film wire.

4. The monolithic reusable microwire assembly of claim 1, wherein the substrate adhesion layer comprises $SiO_2$.

5. The monolithic reusable microwire assembly of claim 1, wherein the thin film wire adhesion layer comprises titanium or chromium.

6. The monolithic reusable microwire assembly of claim 1, wherein the diffusion barrier layer comprises SiN.

7. The monolithic reusable microwire assembly of claim 1, wherein the thin film wire comprises at least one of copper, aluminum, chromium, and niobium.

8. The monolithic reusable microwire assembly of claim 1, further comprising an adhesion layer, an etch stop layer, or a combination thereof positioned between the thin film wire and the thermally and electrically insulating barrier.

9. The monolithic reusable microwire assembly of claim 8, wherein the adhesion layer comprises titanium, wherein the etch stop layer comprises at least one of gold, silver and platinum, and wherein the thermally and electrically insulating barrier comprises a SiN layer, a $SiO_2$ layer, or a combination thereof.

10. The monolithic reusable microwire assembly of claim 1, wherein the roughness-reducing layer has a surface roughness of less than or equal to 20 nm.

11. A monolithic spintronic device, comprising,
    a monolithic reusable microwire assembly, comprising:
        a substrate;
        an electrically conductive thin-film wire formed on the substrate, said thin film wire having a narrow segment forming an active area;
        a thermally and electrically insulating barrier formed on the electrically conductive thin-film wire; and
        a roughness-reducing layer formed on the thermally and electrically insulating barrier, said roughness-reducing layer having a surface roughness of less than or equal to 20 nm; and
    a thin film device formed on the monolithic reusable microwire assembly to form the monolithic spintronic device, and wherein the thin-film device is positioned directly above the active area of the thin film wire.

12. The monolithic spintronic device of claim 11, wherein the thin-film device is at least one of an organic light-emitting diode (OLED), light emitting diode, magnetometer, solar cell, resistor, and capacitor.

13. The monolithic spintronic device of claim 12, wherein the OLED comprises a hole injector layer and an emitting layer.

14. The monolithic spintronic device of claim 13, wherein the hole injector layer comprises poly(styrene-sulfonate)-doped poly(3,4-ethylenedioxythiophene) (PEDOT:PSS) and wherein the emitting layer comprises at least one of super-yellow poly(phenylene-vinylene) (SY-PPV), MEH-PPV (partially and fully deuterated), PCBM, $P_3HT$, $Alq_3$, amorphous silicon, SiC and PEDOT:PSS.

15. The monolithic spintronic device of claim 11, wherein the thin film device has a width of from 20 nm to 400 nm.

16. The monolithic spintronic device of claim 11, further comprising a cathode formed on the thin film device.

17. The monolithic spintronic device of claim 11, further comprising an electrical contact layer formed between the thin-film device and the monolithic thin-film microwire assembly.

18. A method of manufacturing a monolithic microwire assembly, comprising:
    depositing an electrically conductive thin film microwire on a substrate;
    shaping the thin film microwire to have a narrow segment forming an active area of the thin film microwire; and
    depositing an electrical and thermal insulation barrier on the thin film microwire;
    depositing a roughness-reducing layer on the electrical and thermal insulation barrier to achieve a surface roughness of less than 5 nm.

19. The method of claim 18, further comprising forming an oxide layer on the substrate prior to depositing the electrically conductive thin film microwire on the substrate.

20. The method of claim 19, further comprising depositing a diffusion barrier layer on the oxide layer prior to depositing the electrically conductive thin film microwire on the substrate.

21. The method of claim 20, wherein the diffusion barrier layer comprises SiN.

22. The method of claim 20, further comprising depositing a thin film microwire adhesion layer on the diffusion barrier layer.

23. The method of claim 22, wherein the thin film microwire adhesion layer comprises titanium.

24. The method of claim 18, further comprising depositing a thin film microwire adhesion layer on the thin film microwire.

25. The method of claim 18, further comprising depositing an etch stop layer on the thin film microwire or intervening thin film microwire adhesion layer prior to shaping the thin film microwire.

26. The method of claim 25, further comprising depositing an etch stop adhesion layer on the etch stop layer.

27. The method of claim 18, wherein shaping the thin film microwire comprises photolithography, wet etching, or a combination thereof.

28. The method of claim 18, further comprising etching an exposed surface of the electrical and thermal insulation barrier to reduce surface roughness to less than or equal to a thickness of the top layer.

* * * * *